(12) United States Patent
Simonton et al.

(10) Patent No.: US 8,246,571 B2
(45) Date of Patent: Aug. 21, 2012

(54) DRUG STORAGE AND DELIVERY DEVICE HAVING A RETAINING MEMBER

(75) Inventors: Thomas Andrew Simonton, Memphis, TN (US); William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 245 days.

(21) Appl. No.: 12/861,857

(22) Filed: Aug. 24, 2010

(65) Prior Publication Data

US 2012/0053561 A1    Mar. 1, 2012

(51) Int. Cl.
*A61F 13/20* (2006.01)
*A61M 31/00* (2006.01)

(52) U.S. Cl. .............. 604/60; 604/57; 604/15; 604/506

(58) Field of Classification Search .............. 604/11–15, 604/57, 59, 60, 285–288, 506
See application file for complete search history.

(56) References Cited

U.S. PATENT DOCUMENTS

| | | | |
|---|---|---|---|
| 4,820,267 A * | 4/1989 | Harman | 604/60 |
| 5,725,508 A | 3/1998 | Chanoch et al. | |
| 6,069,129 A | 5/2000 | Sandberg et al. | |
| 6,179,862 B1 | 1/2001 | Sawhney | |
| 6,287,588 B1 | 9/2001 | Shih et al. | |
| 6,331,311 B1 | 12/2001 | Brodbeck et al. | |
| 6,428,804 B1 | 8/2002 | Suzuki et al. | |
| 6,461,631 B1 | 10/2002 | Dunn et al. | |
| 6,565,541 B2 | 5/2003 | Sharp | |
| 6,589,549 B2 | 7/2003 | Shih et al. | |
| 6,630,155 B1 | 10/2003 | Chandrashekar et al. | |
| 6,632,457 B1 | 10/2003 | Sawhney | |
| 6,773,714 B2 | 8/2004 | Dunn et al. | |
| 7,081,123 B2 | 7/2006 | Merboth et al. | |
| 2002/0009454 A1 | 1/2002 | Boone et al. | |
| 2002/0090398 A1 | 7/2002 | Dunn et al. | |
| 2004/0072799 A1 | 4/2004 | Li et al. | |
| 2004/0082540 A1 | 4/2004 | Hermida Ochoa | |
| 2004/0214793 A1 | 10/2004 | Hermida Ochoa | |
| 2005/0142163 A1 | 6/2005 | Hunter et al. | |
| 2005/0186261 A1 | 8/2005 | Avelar et al. | |
| 2005/0197293 A1 | 9/2005 | Mellis et al. | |

(Continued)

FOREIGN PATENT DOCUMENTS

KR    10-2006-0120103 A    11/2006

(Continued)

OTHER PUBLICATIONS

International Search Report and Written Opinion for PCT/2011/048205 the counterpart application mailed on Mar. 20, 2012.

*Primary Examiner* — Christopher D Koharski
*Assistant Examiner* — Leah Stohr

(57) ABSTRACT

Drug depot storage and delivery devices and methods for delivering a drug depot to a site beneath the skin of a patient are provided. In various embodiments, the drug depot storage and delivery device comprises a retaining member that in an open position allows delivery of the drug depot from the drug cartridge to the target tissue site. In various embodiments, the drug depot storage and delivery device comprises a retaining member that in a closed position reduces or prevents delivery of the drug depot from the drug cartridge to the target tissue site.

20 Claims, 8 Drawing Sheets

U.S. PATENT DOCUMENTS

| | | |
|---|---|---|
| 2005/0288620 A1 | 12/2005 | Shippert |
| 2006/0148903 A1 | 7/2006 | Burch et al. |
| 2006/0153815 A1 | 7/2006 | Seyda et al. |
| 2006/0161114 A1 | 7/2006 | Perot et al. |
| 2006/0189944 A1 | 8/2006 | Campbell et al. |
| 2007/0021358 A1 | 1/2007 | Edelman et al. |
| 2007/0066864 A1 | 3/2007 | Forde |
| 2007/0104769 A1 | 5/2007 | Feng et al. |
| 2007/0156180 A1 | 7/2007 | Jaax et al. |
| 2007/0202074 A1 | 8/2007 | Shalaby |
| 2007/0233038 A1 | 10/2007 | Pruitt et al. |
| 2007/0243225 A1 | 10/2007 | McKay |
| 2007/0243228 A1 | 10/2007 | McKay |
| 2008/0009830 A1 | 1/2008 | Fujimoto et al. |
| 2008/0038351 A1 | 2/2008 | Beals et al. |
| 2008/0091207 A1 | 4/2008 | Truckai et al. |
| 2009/0131908 A1 | 5/2009 | McKay |
| 2010/0106132 A1 | 4/2010 | Simonton |
| 2010/0106137 A1 | 4/2010 | Simonton et al. |

FOREIGN PATENT DOCUMENTS

| | | |
|---|---|---|
| WO | 03005961 A2 | 1/2003 |

* cited by examiner

DRUG STORAGE AND DELIVERY DEVICE HAVING A RETAINING MEMBER

BACKGROUND

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Recently, drug depots have been developed which allow a drug to be introduced or administered to sites beneath the skin of a patient so that the drug is slowly released over a long period of time. Such drug depots allow the drug to be released from the depot in a relatively uniform dose over weeks, months or even years. This method of administering drugs is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

Previously, drug depots and other types of implants have been inserted into the treatment site beneath the skin by use of a trocar device, which is a two-piece device that includes a cannula and an obdurator. The trocar device requires an incision to be made through the skin at the site of implant of the drug depot using a separate instrument (e.g., scalpel). A cannula and obdurator are inserted together through the skin at the incision site. Next, the obdurator is withdrawn, leaving the cannula in place as a guide for inserting the drug depot. The drug depot is inserted through the cannula, and the obdurator is used to push the implant to the end of the cannula. The cannula and obdurator are then withdrawn completely, leaving the implant in place beneath the skin.

Typically, trocar devices are used to implant drug depots subcutaneously over a large area (e.g., 2-2.5 inches), with a typical drug depot in the order of 1½ inches long. Thus, the trocar device is not suitable for many treatment sites because it lacks precision and may cause additional trauma to the tissue surrounding the site of implant.

Other drug depot devices have been developed to simplify implanting the drug depots. These devices have a handle for one-handed implantation of the drug depot, a needle containing the drug depot to be implanted and a rod positioned within the needle for pushing the drug depot out of the needle. Once the needle containing the drug depot has been inserted at the site of implant, a spring loaded trigger on the handle is activated which causes the needle to be automatically withdrawn by a spring leaving the implanted drug depot in place. Unfortunately, it is not possible to control the motion of the needle in these devices because the needle will automatically retract upon activation of the trigger. The complex spring loaded propelling system and trigger of these devices increase the chances that the device will jam and fail to eject the drug depot when required.

Conventional needle and syringe devices have been used to implant a drug depot to sites such as, for example, the epidural space. These devices typically utilize a syringe preloaded with the drug depot and an epidural needle. The needle is inserted through the skin, supraspinus ligament, intraspinus ligament, ligamentum flavum and then into the epidural space. The drug depot is delivered through the needle to the epidural space using the syringe plunger.

Often, conventional needle and syringe devices do not easily allow controlled and precision implant of the drug depot. For example, sometimes with conventional needle and syringe devices, drug depots can prematurely be dispensed by these devices or they may be difficult for the user to handle them.

New drug depot devices and methods are needed, which can easily allow accurate and precise implantation of a drug depot with minimal physical and psychological trauma to a patient. Drug depot delivery devices and methods that reduce or inhibit drug depots from prematurely being dispensed or falling out of the drug depot device are also needed.

SUMMARY

New drug depot devices, which can easily allow accurate and precise implantation of one or more drug depots with minimal physical and psychological trauma to a patient are provided. One advantage of the drug depot device is that it allows the user to dispense multiple doses of the drug in sequence.

The drug depot device, in various embodiments, includes a drug cartridge containing one or more drug depots that has the advantages of easily being sterilized. The drug cartridge is coupled to a housing, and a plunger is moved through the housing, and the drug cartridge to facilitate the release of the drug depot from the drug cartridge. The device comprises a retaining member movably attached to the drug cartridge that prevents delivery of the drug depot when the retaining member is in a closed position and allows delivery of the drug depot when the retaining member is in a closed position.

In some embodiments, the ring member comprises a safety ring and reduces or prevents the drug depot from being prematurely dispensed or it falling out of the device. In some embodiments, the storage and delivery device of the current application can be used as the primary packaging for the drug depots because they are contained within the device.

In a first embodiment, there is a device for storing a drug depot, the device comprising: a housing having a first end configured to receive a plunger, a second end configured to receive a cannula, an opening disposed in the housing between the first and second ends and configured to receive a drug cartridge containing a drug depot, and a delivery channel disposed within the housing and configured to receive the plunger and the drug depot from the drug cartridge, the drug cartridge having an opening, recess or projection and comprising a channel to receive the drug depot and the plunger and align with the delivery channel of the housing to allow delivery of the drug depot from the drug cartridge by the plunger; and a ring member configured to attach to the housing and the opening, recess or projection of the drug cartridge to prevent alignment of the channel of the drug cartridge with the delivery channel of the housing so as to store the drug depot.

In a second embodiment, there is a device for delivering a drug depot to a site beneath the skin of patient, the device comprising: a housing having a first end configured to receive a plunger, a second end configured to receive a cannula, an opening disposed in the housing between the first and second ends, and a delivery channel disposed within the housing and configured to receive the plunger; a drug cartridge configured to be disposed in the opening of the housing between the first and second ends of the housing, the drug cartridge having a mating member and comprising a drug depot disposed in a channel of the drug cartridge, the channel of the drug cartridge configured to receive at least a tip of the plunger and align with the delivery channel of the housing; and a ring member configured to attach to the housing and mate with the mating member of the drug cartridge to prevent alignment of the channel of the drug cartridge with the delivery channel of the housing when the ring member is in a closed position so as to allow storage of the drug depot, and the ring member configured to allow alignment of the channel of the drug cartridge with the delivery channel of the housing when the ring is in an open position so as to allow delivery of the drug depot from the drug cartridge by the plunger.

In a third embodiment, there is a method of delivering a drug depot to a target tissue site beneath the skin, the method comprising: inserting a sheath at the target tissue site, the sheath having a proximal end and a distal end, the proximal end of the sheath having an opening to receive a drug depot, the distal end of the sheath having an opening for passage of the drug depot; inserting a cannula into the sheath, the cannula connected to a drug delivery device, the drug delivery device having a housing having a first end configured to receive a plunger, a second end configured to receive a cannula, an opening disposed in the housing between the first and second ends, and a delivery channel disposed within the housing and configured to receive the plunger; a drug cartridge configured to be disposed in the opening of the housing between the first and second ends of the housing, the drug cartridge having a mating member and comprising a drug depot disposed in a channel of the drug cartridge, the channel of the drug cartridge configured to receive at least a tip of the plunger and align with the delivery channel of the housing; and a ring member configured to attach to the housing and mate with the mating member of the drug cartridge to prevent alignment of the channel of the drug cartridge with the delivery channel of the housing when the ring member is in a closed position so as to allow storage of the drug depot, and the ring member configured to allow alignment of the channel of the drug cartridge with the delivery channel of the housing when the ring is in an open position so as to allow delivery of the drug depot from the drug cartridge by the plunger; moving the ring member to the open position; and moving the tip of the plunger so as to cause delivery of the drug depot from the drug cartridge into at least the cannula or sheath and to the target tissue site by moving the plunger.

In a fourth embodiment, there is a device for delivering a drug depot to a site beneath the skin of patient, the device comprising: a housing having a first end configured to receive a plunger, a second end configured to receive a cannula, an opening disposed in the housing between the first and second ends, and a delivery channel disposed within the housing and configured to receive the plunger; and a drug cartridge slidable within the opening of the housing between the first and second ends of the housing, the drug cartridge having a drug depot disposed in a channel of the drug cartridge, the channel of the drug cartridge configured to receive at least a tip of the plunger and align with the delivery channel of the housing to deliver the drug depot and the drug cartridge comprising at least two mating members that mate with the housing, one mating member being longer than the other and preventing the drug cartridge from falling out of the housing.

In a fifth embodiment, there is a device for delivering a drug depot to a site beneath the skin of patient, the device comprising: a housing having a first end configured to receive a plunger, a second end configured to receive a cannula, an opening disposed in the housing between the first and second ends, and a delivery channel disposed within the housing and configured to receive the plunger; and a drug cartridge slidable within the opening of the housing between the first and second ends of the housing, the drug cartridge having a drug depot disposed in a channel of the drug cartridge, the channel of the drug cartridge configured to receive at least a tip of the plunger and align with the delivery channel of the housing to deliver the drug depot and the drug cartridge comprising a mating member; and a ring member configured to attach to the housing and mate with the mating member of the drug cartridge to hold the drug cartridge in position to reduce or prevent alignment of the channel of the drug cartridge with the delivery channel.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
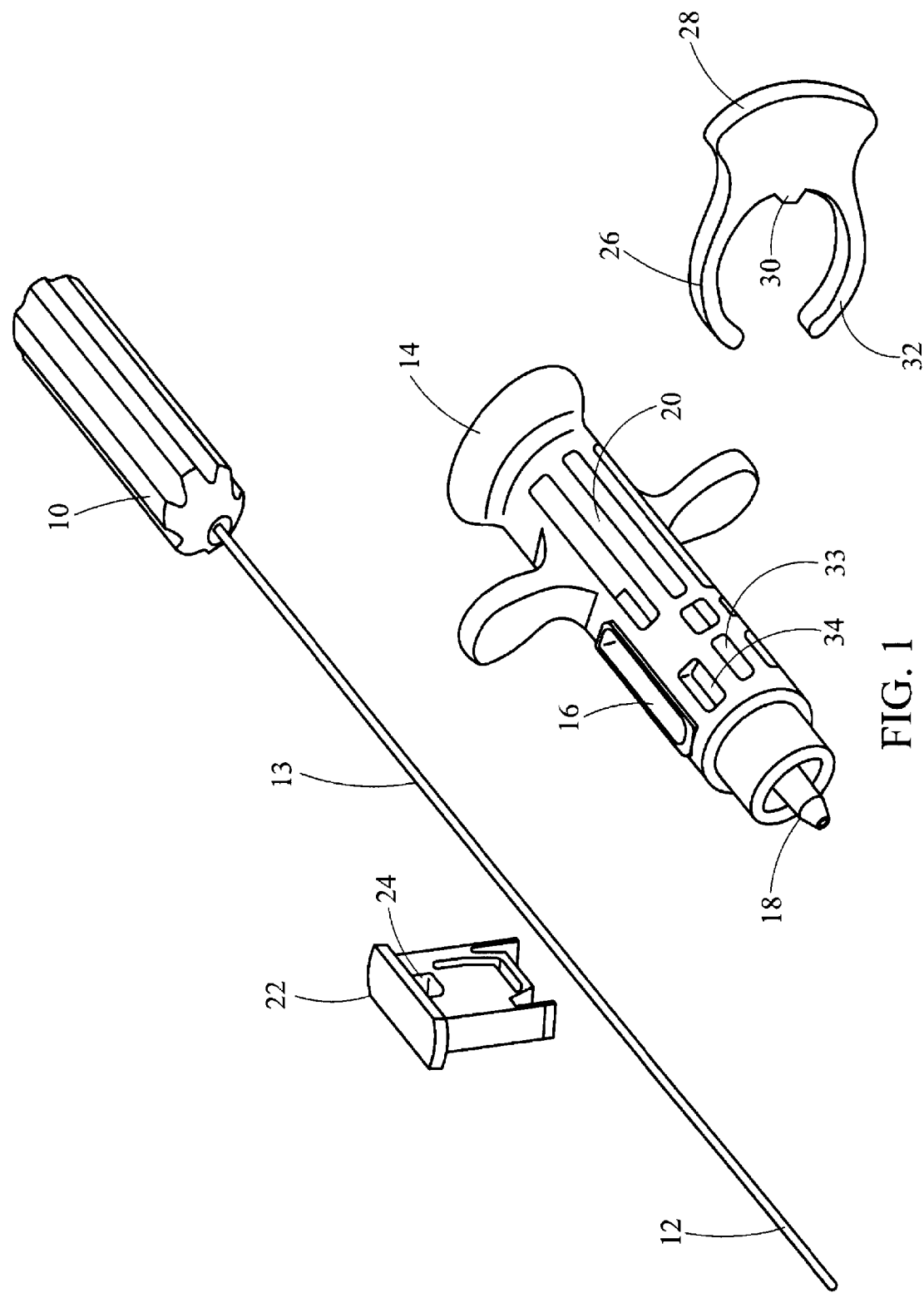
FIG. 1 illustrates a top view of an embodiment of an unassembled drug depot storage and/or delivery device having a housing, a plunger, a drug cartridge containing a drug depot, and a retaining member movable in an open and closed position to lock the drug cartridge and store the drug depot.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

Drug Storage and Delivery Device

New drug depot devices, which can easily allow accurate and precise implantation of a drug depot with minimal physical and psychological trauma to a patient are provided. One advantage of the drug depot device is that it allows the user to dispense multiple doses of the drug in sequence.

The drug depot device, in various embodiments, includes a drug cartridge containing one or more drug depots that has the advantages of easily being sterilized. The drug cartridge is coupled to a housing, and a plunger is moved through the housing, and the drug cartridge to facilitate the release of the drug depot from the drug cartridge. The device comprises a retaining member (e.g., ring member, clip, etc.) movably attached to the drug cartridge that prevents delivery of the drug depot when the ring is in a closed position and allows delivery of the drug depot when the retaining member (e.g., ring member, clip, etc.) is in a closed position.

In some embodiments, the retaining member comprises a safety ring and reduces or prevents the drug depot from being prematurely dispensed or it falling out of the device. In some embodiments, the storage and delivery device of the current application can be used as the primary packaging for the drug depots because they are contained within the device.

In one embodiment, there is a device for storing a drug depot, the device comprising: a housing having a first end configured to receive a plunger, a second end configured to receive a cannula, an opening disposed in the housing between the first and second ends and configured to receive a drug cartridge containing a drug depot, and a delivery channel disposed within the housing and configured to receive the plunger and the drug depot from the drug cartridge, the drug cartridge having an opening, recess or projection and comprising a channel to receive the drug depot and the plunger and align with the delivery channel of the housing to allow delivery of the drug depot from the drug cartridge by the plunger; and a retaining member (e.g., ring member, clip) configured to attach to the housing and the opening, recess or projection of the drug cartridge to prevent alignment of the channel of the drug cartridge with the delivery channel of the housing so as to store the drug depot.

FIG. 1 illustrates a top view of an embodiment of an unassembled drug depot storage and/or delivery device comprising a housing 20 having a first end 14 and a second end 18 and an opening 16. The first end 14 of the housing is configured to receive at least the tip of the plunger 12. The plunger has a handle 10 that will contact the first end when the plunger is in the extended position. The second end 18 of the housing is configured to receive at least the tip of the plunger 12 and allow passage of the drug depot out through it. This can be accomplished by sliding the plunger handle 10 in the forward direction, which allows plunger body 13 and tip 12 to slide through an opening in the first end 14 and an opening in the second end 18. Opening 16 of the housing 20 is configured to receive a drug cartridge 22 that contains one or more drug depots. The drug cartridge has a mating member 24, which can be an opening, recess or projection. In the embodiment shown, the mating member 24 is shown as an opening that is configured to receive a complementary mating member, which can be an opening, recess or projection of a retaining member 28 (e.g., ring member, safety clip or safety ring). The retaining member 28 is configured to reduce or prevent movement of the drug cartridge 22 and attach to the housing by mating openings, recesses or projections. In this way, retaining member 28 functions as a safety clip or safety ring and prevents or reduces the chance that the drug cartridge 22 will move in a position that would allow the drug depots to prematurely discharge from the housing or fall out of the drug cartridge. The retaining member 28 ring also reduces or prevents the chances that the drug cartridge 22 will fall out of the housing 20.

In the embodiment shown, the retaining member 28 comprises projections or arms 26 and 32 and center projection 30. The retaining member can be removably attached to the housing. For example, one arm 32 attaches to the housing and the second arm 26 fits within mating member 24 of the drug cartridge 22 by passing through mating member 24 and projection 30 of retaining member mates with recess 33 of the housing. In this way, retaining member 28 is in a closed position which maintains drug cartridge 22 in a closed position so that the drug depots remain in the cartridge and the drug depots cannot be dispensed. Therefore, retaining member 28 functions as a safety ring and prevents or reduces the chance that the drug cartridge 22 will move in a position that would allow the drug depots to prematurely discharge from the housing or fall out of the drug cartridge. The safety ring also reduces or prevents the chances that the drug cartridge 22 will fall out of the housing 20. In the embodiment shown, the retaining member 28 has a diameter that is smaller than the housing and the retaining member can be pushed onto housing 20, which forces arms 26 and 32 to fit around the housing. This can be a force-fit, friction fit, snap fit type, or other type of coupling means.

The retaining member 28 is rotatable around the axis of the housing 20 (e.g., rotatable 45, 75, 90, 120, or 180 degrees) and the user can rotate the retaining member around housing 20 and the projection 30 will snap or fit snuggly into recess 34 and the arms 26 and 32 will enclose around the housing 20. Therefore, the retaining member will be held in position and can rotate into an open position, which allows the drug cartridge 22 to slide further into opening 16 or, instead, in a closed position, where arm 26 will pass through mating member 24, which locks or prevents the drug cartridge 22 from moving. In this closed position or containment position, the drug cartridge 22 will store or contain the drug depot. Although the retaining member 28 is shown as a ring or clip, it will be understood that the retaining member can be any structure and shape that prevents or reduced movement of the drug cartridge in the housing. For example, the retaining member can be a ring, clip, stick, plate, shaft, wand, board, bar, pin or other structure that can attach to the housing and contact the cartridge to hold it in position. The retaining member can be rounded or flat or elongated.

Figure 2:
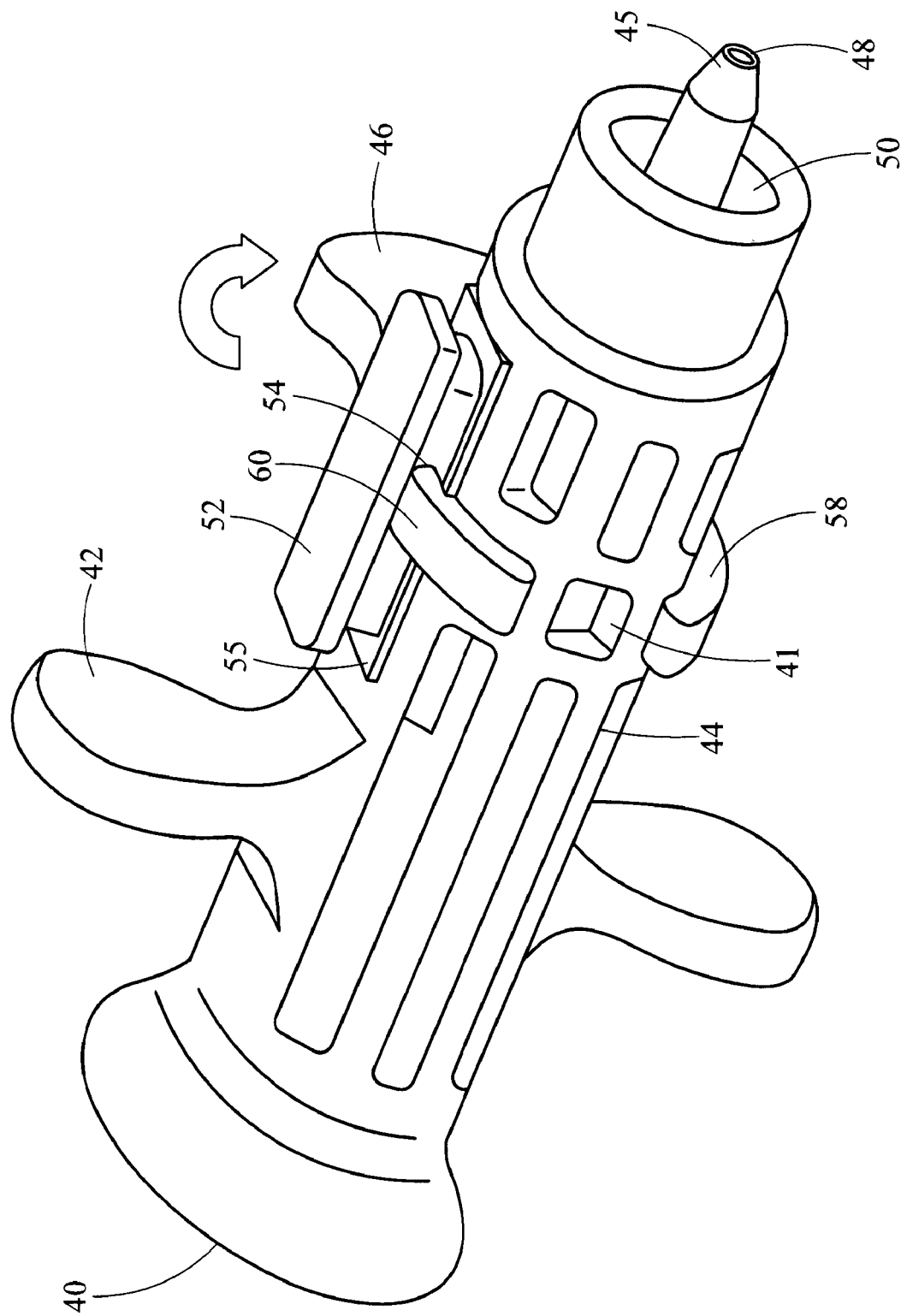
FIG. 2 illustrates a top view of an embodiment of a partially assembled drug depot storage and/or delivery device having a housing, a drug cartridge containing a drug depot attached to the housing, and a retaining member (e.g., ring member) attached to the housing, which is shown in a closed position to lock the drug cartridge to the housing and store the drug depot.

FIG. 2 illustrates a top view of an embodiment of a partially assembled drug depot storage and/or delivery device comprising a housing 44 having a first end 40 and a second end 50 and an opening. The first end 40 of the housing is configured to receive at least the tip and body of a plunger. The plunger will contact the first end when the plunger is in the extended position. The second end 50 of the housing is configured to receive at least the tip of the plunger and allow passage of the drug depot out through it. This can be accomplished by sliding the plunger in the forward direction, which allows plunger body and tip to slide through an opening in the first end 40 and an opening in the second end 48. The housing at the second end is configured to be attached to a cannula or needle via a fitting means 45, which can be a snap fitting, a friction fitting, or a leur fitting. The housing has an opening configured to receive drug cartridge 52, which is shown in this embodiment, partially slid into the opening of the housing. The drug cartridge 52 contains one or more drug depots. The drug cartridge 52 has a mating member 54, which is shown as an opening that is configured to receive a complementary mating member, which can be an opening, recess or projection of a ring member or safety ring 46. The ring member 46 is configured to reduce or prevent movement of the drug cartridge 52 and attach to the housing by mating openings, recesses or projections. In this way, ring member 46 functions as a safety ring and prevents or reduces the chance that the drug cartridge 52 will move in a position that would allow the drug depots to prematurely discharge from the housing or fall out of the drug cartridge. The safety ring also reduces or prevents the chances that the drug cartridge 52 will fall out of the housing 44.

In the embodiment shown, the ring member 46 comprises upper projection or arm 60 and lower projection or arm 58 that is removably attach to the housing. For example, lower projection or arm 58 attaches to the housing. This may be by a complementary recess, opening or projection in the housing (shown as a recess 41) that allows the arm 58 to friction fit or snap fit into a complementary mating member of the housing. The upper arm 60 of the ring member fits within mating member 54 of the drug cartridge 52 by passing through mating member 54 and the arm may have additional openings, recesses and/or projections that allow the arm to mate with the housing. The surface 55 is primarily for ensuring proper alignment of the cartridge so the drug depot is aligned with the through hole openings 40 and 48 of the delivery channel. The surface 55 mates with the undersurface of 52, which allows upper arm 60 to attach to it. In the embodiment shown, ring member 46 is in a closed position which maintains drug cartridge 52 in a closed position so that the drug depots remain in the cartridge and, therefore, the drug depots cannot be dispensed. Therefore, ring member 46 functions as a safety ring and prevents or reduces the chance that the drug cartridge 52 will move in a position that would allow the drug depots to prematurely discharge from the housing or fall out of the drug cartridge. The safety ring also reduces or prevents the chances that the drug cartridge 52 will fall out of the housing 44. The device can then be easily package this way and the user will know that the device not only contains the drug depot, but also has not deployed the depots into delivery channel.

In the embodiment shown, the safety ring 46 has a diameter that is smaller than the housing and the safety ring is pushed onto housing 44, which forces arms 58 and 60 to fit around the housing. This can be a force-fit, friction fit, snap fit, or other type of coupling means. In some embodiments, the safety ring 46 can have a diameter that is larger than the housing for ease of maneuverability and can be attached to the housing via multiple coupling means.

The safety ring 46 is rotatable around the housing 44 (e.g., rotatable by 45, 75, 90, 120, or 180 degrees around the axis of the housing) and the user can rotate the safety ring around housing 44 and the upper arm 60 will have a recess 54 that allows it to snap or fit snuggly into lip 55 of the housing allowing upper arm 60 and lower arm 58 to enclose around the housing. Therefore, the safety ring will be held in position and can rotate into an open position by rotating the safety ring 46 in away from the drug cartridge and in the direction shown by the circular arrow, which allows the drug cartridge 52 to further slide into opening of the housing to allow delivery of the drug depot.

In the embodiment shown in FIG. 2, the device is in the closed position, where upper arm 60 passes through mating member 54, which locks or prevents the drug cartridge 52 from moving upward, downward, and/or side to side. In this closed position, the drug cartridge 52 will store or contain the drug depot and the drug depot can not be delivered out of the housing as the channel of the drug depot and the delivery channel of the housing (shown in FIGS. 4) will not be aligned. The housing may also have grips 42 for the user to hold the housing and connect the cannula, needle, and/or plunger to it at fitting 48. The grips also allow easy angling of the device.

Figure 3:
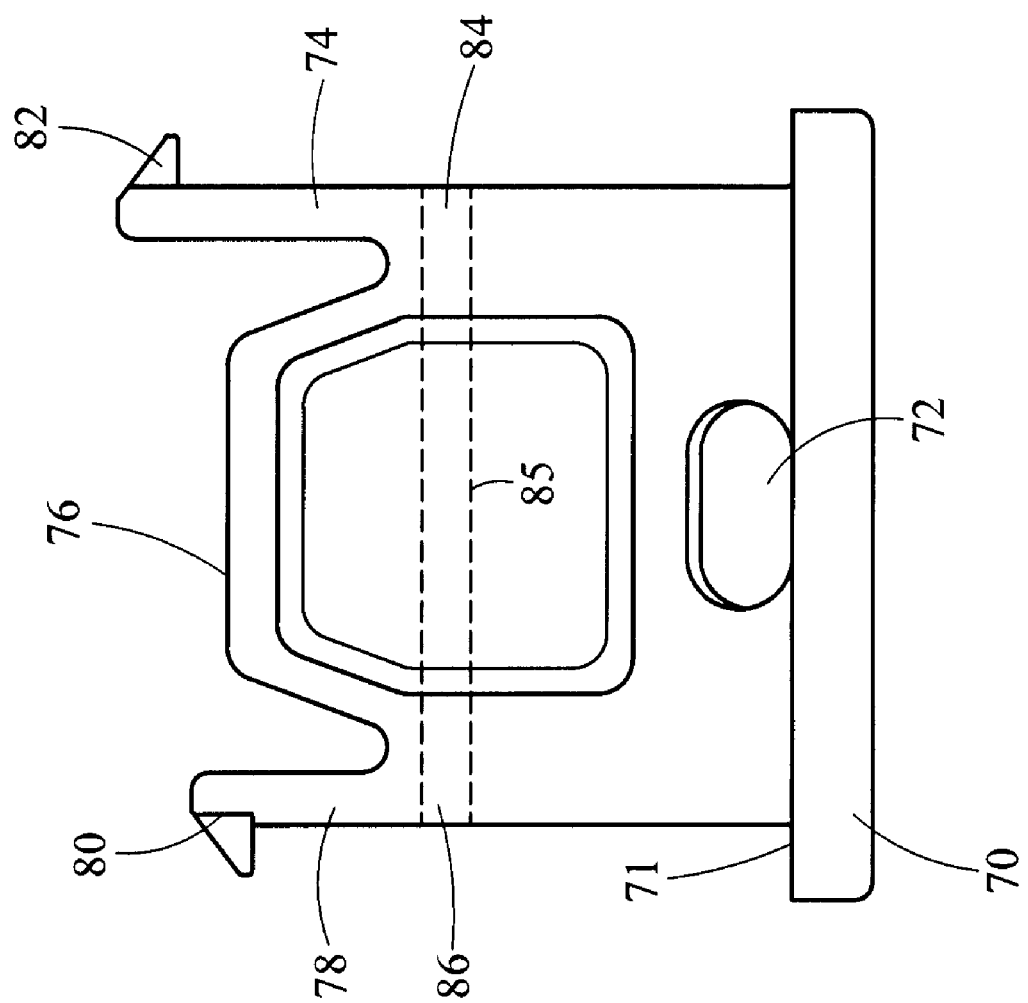
FIG. 3 illustrates a side sectional view of an embodiment of a drug cartridge that contains the drug depot.

FIG. 3 illustrates a side sectional view of an embodiment of a drug cartridge 70 that contains one or more drug depot in a channel 85. The channel 85 runs horizontally through the drug cartridge and is a diameter that is larger than the plunger so that the plunger can pass through first opening 84 in the channel when pushed and cause the one or more drug depots to be pushed by the plunger out of the cartridge at second opening 86 and into the delivery channel of the housing where the plunger can then push the one or more drug depots through the cannula or needle or sheath.

The drug cartridge 70 has lip 71 that contacts the housing. The drug cartridge 70 is configured to slide in the opening of the housing and align the channel of the drug cartridge with the delivery channel of the housing so that at least a portion of the plunger can slide within the delivery channel and the channel of the drug cartridge to allow delivery of the drug depot from the drug cartridge and out of the second end of the housing by pushing the plunger. The drug cartridge can comprise one or more coupling members (e.g., recesses, projections, openings, etc.) that mate with one or more complementary coupling members (e.g., recesses, projections, openings, etc.) of the housing. Shown in FIG. 3 is a projection that has as a slide portion 76 of the drug cartridge that slides into and couples or mates with the opening of the housing.

The drug cartridge 70 also comprises one or more coupling members or mating members (e.g., recesses, projections, openings, etc.) that mate with complementary coupling or mating members (e.g., recesses, projections, openings, etc.) of the ring member or safety ring. In the embodiment shown, the drug cartridge 70 comprises opening 72 that is configured to allow the upper arm or projection of the ring member to couple with it. In this way, the drug cartridge 70 will be locked into position (closed position).

To assist in coupling the drug cartridge 70 to the housing, the drug cartridge comprises a first projection 74 and a second projection 78 configured to mate with a first complementary recess and a second complementary recess of the housing so as to lock the drug cartridge in position when the delivery channel of the housing and the channel 85 of the drug cartridge are aligned. In some embodiments, this will occur when the ring member is removed from mating member 72. The first projection 74 of the drug cartridge can have a length longer than the second projection 78 so as to prevent the drug cartridge from falling out of the housing. In some embodiments, the projections of the drug cartridge 70 can have catches 80 and 82 that mate with complementary mating members of the housing to further prevent the drug cartridge from sliding out of the housing. It will be understood by those or ordinary skill in the art that although projections are shown on the drug cartridge 72, they can also be recesses, openings or other mating members that allow the drug cartridge to be removably attached to the complementary recesses, projections, openings or other mating members of the housing.

Figure 4:
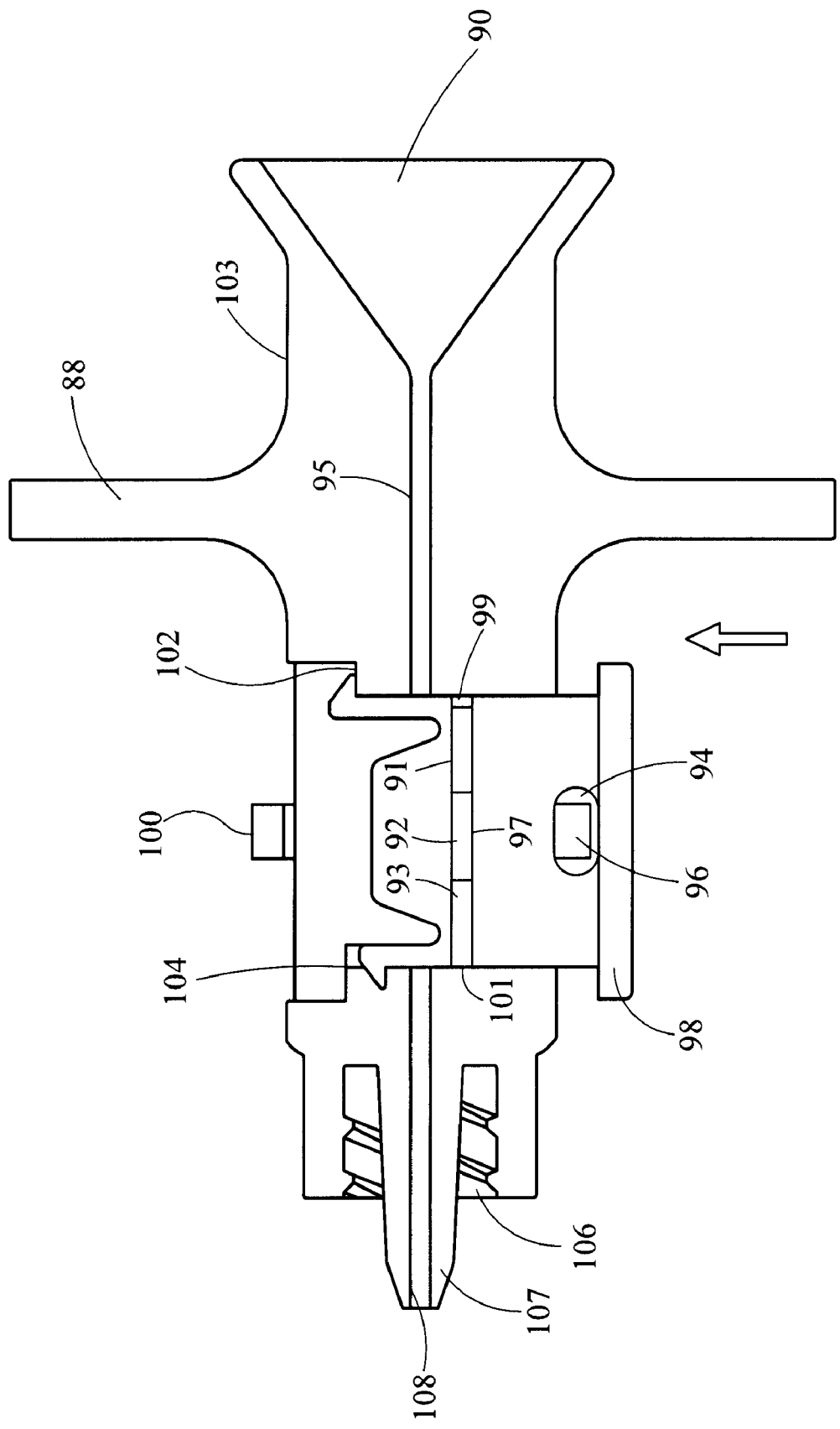
FIG. 4 illustrates a side sectional view of an embodiment of a partially assembled drug depot storage and/or delivery device having a housing, a drug cartridge containing a drug depot attached to the housing that is not aligned with the drug delivery channel, and a ring member attached to the housing, which is shown in a closed position to lock the drug cartridge to the housing and store the drug depot.

FIG. 4 illustrates a side sectional view of an embodiment of a partially assembled drug depot storage and/or delivery device comprising a housing 103 having a first end 90 and a second end 107 and an opening. The first end 90 of the housing 103 is configured to receive at least the tip and body of a plunger. The plunger will contact the first end when the plunger is in the extended position. The second end 107 of the housing is configured to receive at least the tip of the plunger and allow passage of the drug depot out through it. This can be accomplished by sliding the plunger in the forward direction, which allows plunger body and tip to slide through an opening in the first end 90 and an opening in the second end 107. The housing at the second end is configured to be attached to a cannula or needle via a fitting means, which can be a snap fitting, a friction fitting, or a leur fitting (shown in FIG. 4 as 106). The housing has an opening configured to receive drug cartridge 98, which is shown in this embodiment, slid into the opening of the housing. The drug cartridge 98 contains one or more drug depots. In this embodiment, three drug depots 91, 92 and 93 are shown. The drug cartridge 98 has a mating member 94, which is shown as an opening that is configured to receive a complementary mating member 96, which can be an opening, recess or projection of a ring member or safety ring. In this embodiment shown, the complementary mating member 96 of the ring member locks the drug cartridge in the closed position. The ring member is configured to reduce or prevent movement of the drug cartridge 98 and attach to the housing by mating openings, recesses or projections. In this way, ring member functions as a safety ring and prevents or reduces the chance that the drug cartridge 98 will move in a position that would allow the drug depots to prematurely discharge from the housing or fall out of the drug cartridge. The safety ring also reduces or prevents the chances that the drug cartridge 98 will fall out of the housing 103.

In the embodiment shown, the ring member comprises lower projection or arm 96 and upper projection or arm 100 that is removably attach to the housing. The lower arm 96 of the ring member fits within mating member 94 of the drug cartridge 98 by passing through mating member 94 and the arm may have additional openings, recesses and/or projections that allow the arm to mate with the housing.

In the embodiment shown, the ring member is in a closed position which prevents a plunger from passing through the delivery channel portion 95 of the housing and the channel 97 of the drug cartridge because the channel 97 of the drug cartridge is not aligned with the delivery channel portions 95 and 108. Further, the drug cartridge is locked in the housing and prevented from moving upward, downward, and/or side to side. Therefore, the drug depots 91, 92 and 93 are contained within the channel 97 of the drug cartridge by housing portions 101 and 99. In this way, the ring maintains the drug cartridge 98 in a closed position so that the drug depots remain in the cartridge and, therefore, the drug depots cannot be dispensed.

In addition to or in lieu of the ring member, to further hold the drug cartridge 98 in the closed position, recesses or ledges in the housing 102 and 104 are provided that are complementary to the projections or arms of the drug cartridge. At least one of the arms (shown as the longer arm), rests on ledge 102 of the housing and is prevented from falling out of it. Further, shorter arm 104 will catch on to the complementary mating pair of the housing just above it, when the drug cartridge is activated and aligned. In this way recesses, projections or openings in the housing that mate with the complementary recesses, projections or openings of the drug cartridge can prevent it from falling out of the housing. The housing may also have grips 88 for the user to hold the housing and connect the cannula, needle, and/or plunger to it. The grips also allow easy angling of the device.

In the embodiment shown, the delivery channel of the housing 95 and 108 is a larger diameter than the plunger and can be the same, smaller or larger diameter than the channel 97 of the drug cartridge 98. The delivery channel of the housing 95 and 108 can be the same diameter or different from diameter from each other. The delivery channel 95 and 108 of the housing and the channel 97 of the drug cartridge 98 will allow at least the plunger tip and the one or more drug depots to pass through it and out of the housing for delivery. The drug depots 91, 92 and 93 can be aligned in the channel and the user can push the drug depots through the delivery channel 108 of the housing a plunger and out of the housing to deliver the drug depot to the target site. It will be understood by those of ordinary skill in the art that the plunger slides along a longitudinal axis in the channel 97 of the drug cartridge and the drug delivery channel 95 and 108 when the channel of the drug cartridge 98 and the drug delivery channel 95 and 108 are aligned. In some embodiments, the drug cartridge 98 vertically slides (shown by the dark arrow) in the opening of the housing to align channel 97 of the drug cartridge 98 and the drug delivery channel 95 and 108. In this case, the ring member is removed from the housing or rotatable around the housing to remove it from the drug cartridge so as to allow alignment of the channel 97 of the drug cartridge with the drug delivery channel 95 and 108.

Figure 5:
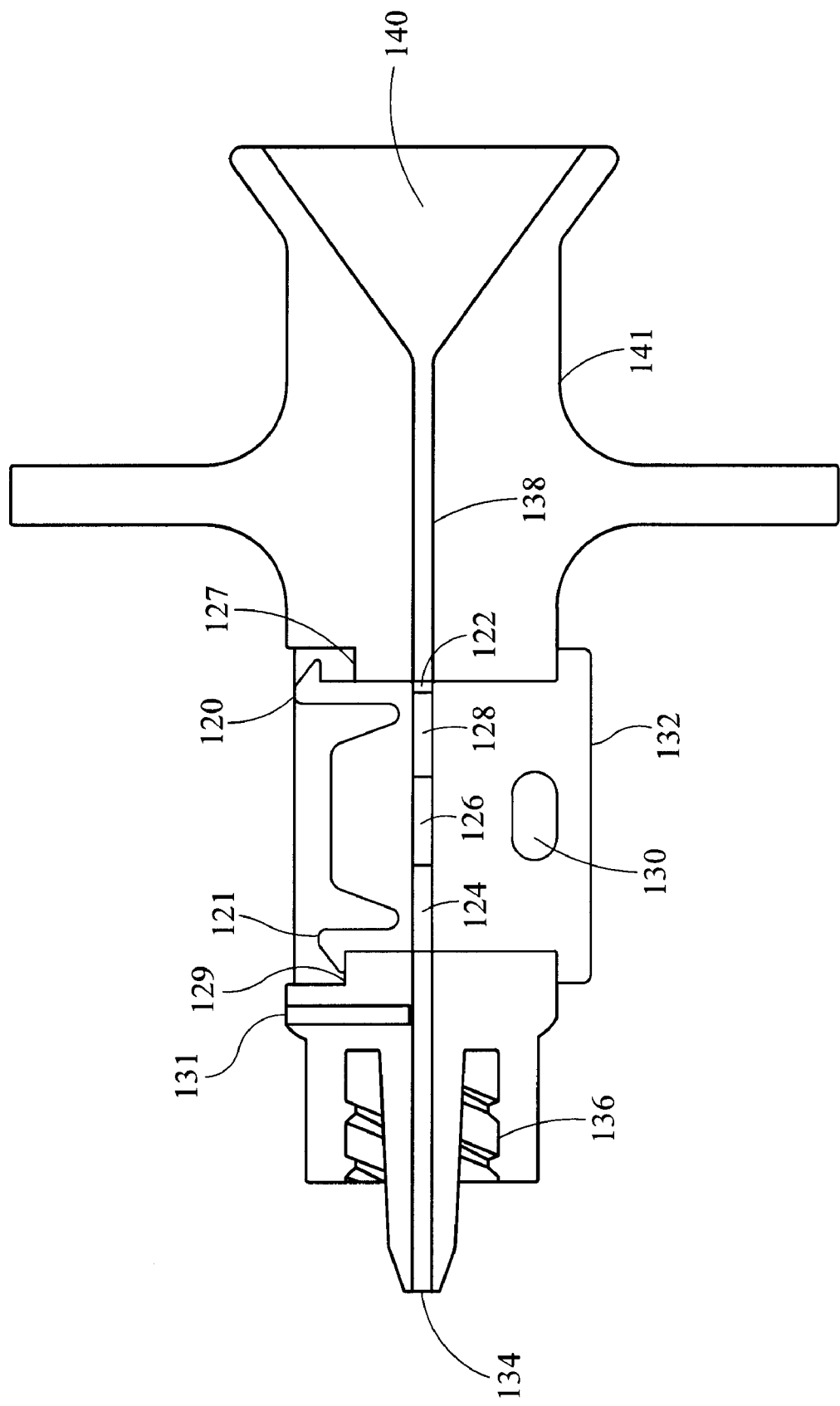
FIG. 5 illustrates a side cross-sectional view of an embodiment of a partially assembled drug depot storage and/or delivery device having a housing, a drug cartridge containing a drug depot attached to the housing that is aligned with the drug delivery channel, and ready for delivery as the retaining member has been removed from the housing or is rotated away from the drug cartridge in an open position.

FIG. 5 illustrates a side sectional view of an embodiment of a partially assembled drug depot storage and/or delivery device comprising a housing 141 having a first end 140 and a second end 134 and an opening having a drug cartridge 132 slid into the opening. The first end 140 of the housing is configured to receive at least the tip and body of a plunger. The plunger will contact the first end when the plunger is in the extended position. The second end 134 of the housing is configured to receive at least the tip of the plunger and allow passage of the drug depot out through it. This can be accomplished by sliding the plunger in the forward direction, which allows plunger body and tip to slide through an opening in the first end 140 and through the delivery channel 138 and through the aligned channel 122 of the drug cartridge, which pushes the drug depots 124, 126, and 128 out of the channel and into the delivery channel of the housing and out second end opening 134. The housing at the second end is configured to be attached to a cannula or needle via a fitting means, which can be a snap fitting, a friction fitting, or a leur fitting (shown in FIG. 5 as 136).

The housing has an opening configured to receive drug cartridge 132, which is shown in this embodiment, slid further into the opening of the housing so that the lip of the drug cartridge contacts the housing. The drug cartridge 132 contains one or more drug depots. In this embodiment, three drug depots 124, 126 and 128 are shown. The drug cartridge 132 has a mating member 130, which is shown as an opening that is configured to receive a complementary mating member, which can be an opening, recess or projection of a ring member or safety ring. In this embodiment shown, the complementary mating member of the ring member has been rotated away from the drug cartridge 132 or is removed from the housing 141 all together. This allows the drug cartridge 132 to be further slid into the housing aligning the channel 122 of the drug cartridge 132 and delivery channel 138 of the housing, which allows the user to push the plunger in a forward direction and deploy the drug depots 124, 126, and 128 out of the second opening 134.

The drug cartridge 132 can comprise mating members that are openings, recesses, and/or projections that mate with complementary openings, recesses, and/or projections of the housing. To hold the drug cartridge 132 in an open position and align the delivery channel 138 of the housing and the channel 122 of the drug cartridge, recesses or ledges in the housing 127 and 129 are provided that are complementary to the projections or arms of the drug cartridge. At least one of the arms (shown as the shorter arm 121), snaps in or rests on ledge 129 of the housing, when the drug cartridge is activated and depots are ready for delivery. The drug cartridge 132 is prevented from falling out of it. In this way recesses, projections or openings in the housing that mate with the complementary recesses, projections or openings of the drug cartridge can prevent it from falling out of the housing as well as keeping the cartridge aligned in the proper position to allow deployment of the drug depots. Longer arm of the drug cartridge 120 is not resting or snapped into ledge 127 of the housing, but acts as a backup catch in the event that shorter arm 121 becomes dislodged from its complementary ledge 129. The longer arm 120 and ledge 127 also allows the drug cartridge to be placed kept in position when the channels are not aligned. This extra feature further prevents the drug cartridge from falling out of the housing. The longer arm 120 when resting or snapped into ledge 127 properly positions the cartridge into the contained position and allows proper positioning for the safety ring 96 in FIG. 4.

In the embodiment shown, the delivery channel of the housing 138 is a larger diameter than the plunger and can be the same, smaller or larger diameter than the channel 122 of the drug cartridge 132. The delivery channel 138 of the housing and the channel 122 of the drug cartridge 132 will allow at least the plunger tip and the one or more drug depots to pass through it and out of the housing for delivery. The drug depots 124, 126 and 128 can be aligned in the channel and the user can push the drug depots through the delivery channel 138 of the housing a plunger and out of the housing to deliver the drug depot to the target site. It will be understood by those of ordinary skill in the art that the plunger slides along a longitudinal axis in the channel 122 of the drug cartridge and the drug delivery channel 138 when the channel of the drug cartridge 132 and the drug delivery channel 138 and 122 are aligned. In some embodiments, the drug cartridge 132 vertically slides in the opening of the housing to align the channel 122 of the drug cartridge 132 and the drug delivery channel 138. In this case, the ring member is removable from the housing or rotatable around the housing to remove it from the drug cartridge so as to allow alignment of the channel 122 of the drug cartridge with the drug delivery channel 138.

In the embodiment shown in FIG. 5, there is an access port 131 that is fluidly connected to delivery channel 134 of the housing and channel 122 of the drug cartridge 132. The port 131 is configured to receive a syringe, needle or cannula, which allows the user to place contrast media into the device for imaging or a pharmaceutical composition to give before, during, or after the one or more drug depots are delivered. The access port 131 can also be used to flush the delivery channel 134 or the channel of the drug cartridge 134 or it can be used to flush the cannula, needle and/or sheath used in drug delivery.

In various embodiments, the access port 131 can be for delivery or removal of liquid material (e.g., NS, LR, D5W, SWFI, blood, etc.). The access port connects to the delivery channel and/or the channel of the drug cartridge. In some embodiments, the access port can be a Y-type connector and allows the user to deliver and withdraw liquid material.

Figure 6:
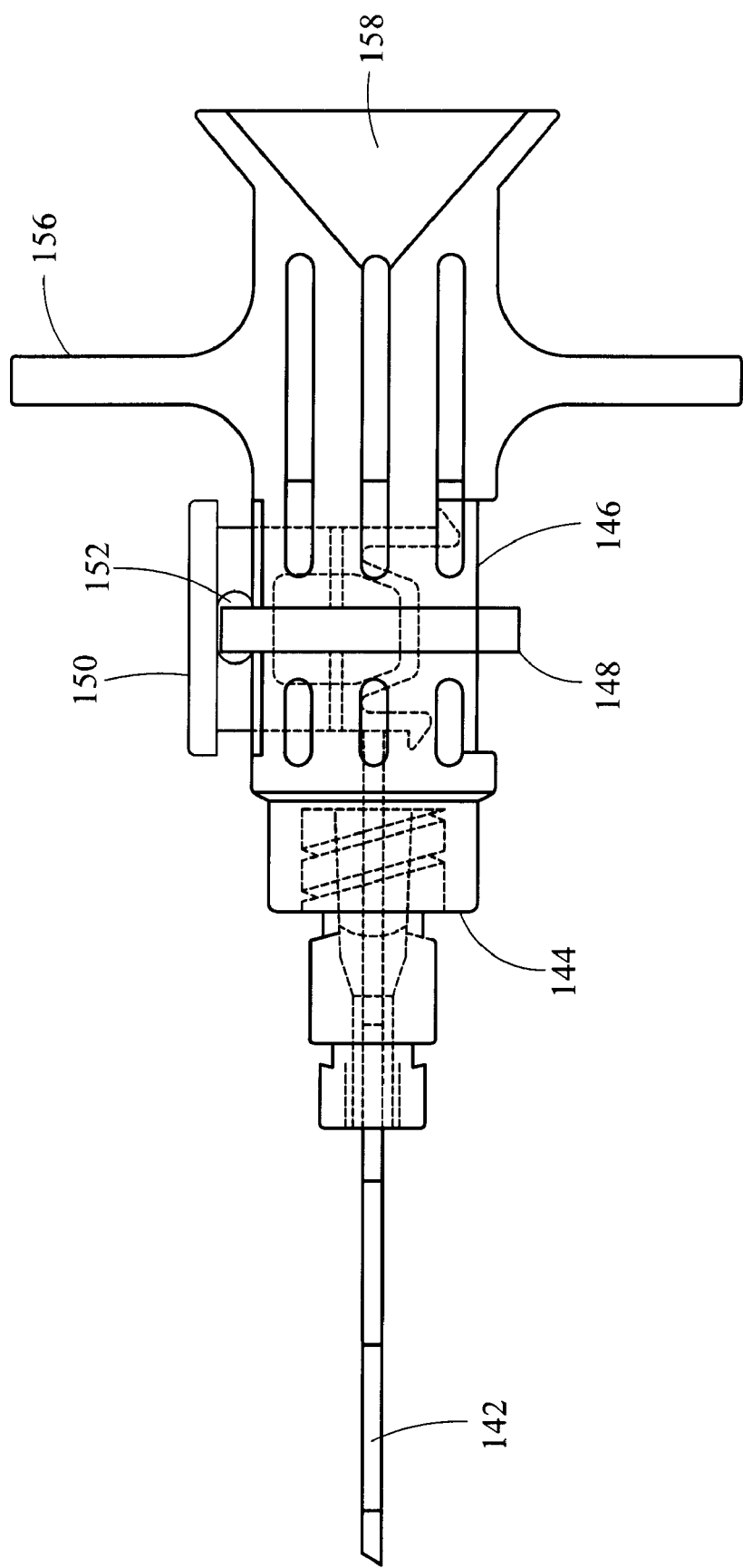
FIG. 6 illustrates a side view of an embodiment of a partially assembled drug depot storage and/or delivery device having a housing, a drug cartridge containing a drug depot attached to the housing that is not aligned with the drug delivery channel, a cannula for delivery of the drug depot and a retaining member (e.g., a ring member) attached to the housing, which is shown in a closed position to lock the drug cartridge to the housing and store the drug depot.

FIG. 6 illustrates a side enlarged view of an embodiment of a partially assembled drug depot storage and/or delivery device comprising a housing 146 having a first end 158 and a second end 144 and an opening. The first end 158 of the housing 146 is configured to receive at least the tip and body of a plunger. The plunger will contact the first end when the plunger is in the extended position. The second end 144 of the housing is configured to receive at least the tip of the plunger and allow passage of the drug depot out through it. This can be accomplished by sliding the plunger in the forward direction, which allows plunger body and tip to slide through an opening in the first end 158 and an opening in the second end 144.

The housing at the second end is configured to be attached to a cannula or needle 142 via a fitting means, which can be a snap fitting, a friction fitting, or a leur fitting. The housing has an opening configured to receive drug cartridge 150, which is shown in this embodiment, slid into the opening of the housing. The drug cartridge 150 contains one or more drug depots stored in it. The drug cartridge 150 has a mating member 152, which is shown as an opening that is configured to receive a complementary mating member 148, which can be an opening, recess or projection of a ring member or safety ring. In this embodiment shown, the complementary mating member 148 of the ring member locks the drug cartridge in the closed position and the drug cartridge is partially slid into the housing, but can not be completely slid into it because the ring member holds it in position and prevents this. More particularly, the ring member is configured to reduce or prevent movement of the drug cartridge 150 and is attach to the housing by mating openings, recesses or projections. In this way, ring member functions as a safety ring and prevents or reduces the chance that the drug cartridge 150 will move in a position that would allow the drug depots to prematurely discharge from the housing or fall out of the drug cartridge. The safety ring also reduces or prevents the chances that the drug cartridge 150 will fall out of the housing 146. In this way, the drug depot storage and delivery device can also be the primary packaging and provide a ready to use delivery device.

In the embodiment shown, the ring member is in a closed position which prevents a plunger from passing through the delivery channel portion of the housing and the channel of the drug cartridge 150 because the channel of the drug cartridge is not aligned with the delivery channel of the housing. Further, the drug cartridge is locked in the housing and prevented from moving upward, downward, and/or side to side. Therefore, the drug depots are contained within the channel of the drug cartridge by the housing. In this way, the ring maintains the drug cartridge 150 in a closed position so that the drug depots remain in the cartridge and, therefore, the drug depots cannot be dispensed.

In the embodiment shown, the opening 152 in the drug cartridge has a diameter that is larger than the ring member 148 so that the ring member fits snug within the housing and the drug cartridge 150 can not fall out. Further, the user will know by the position of the ring member 148 that the drug cartridge 150 has not been used and still can be activated. The housing may also have grips 156 for the user to hold the housing and connect the cannula, needle, and/or plunger to it. The grips also allow easy angling of the device.

Figure 7:
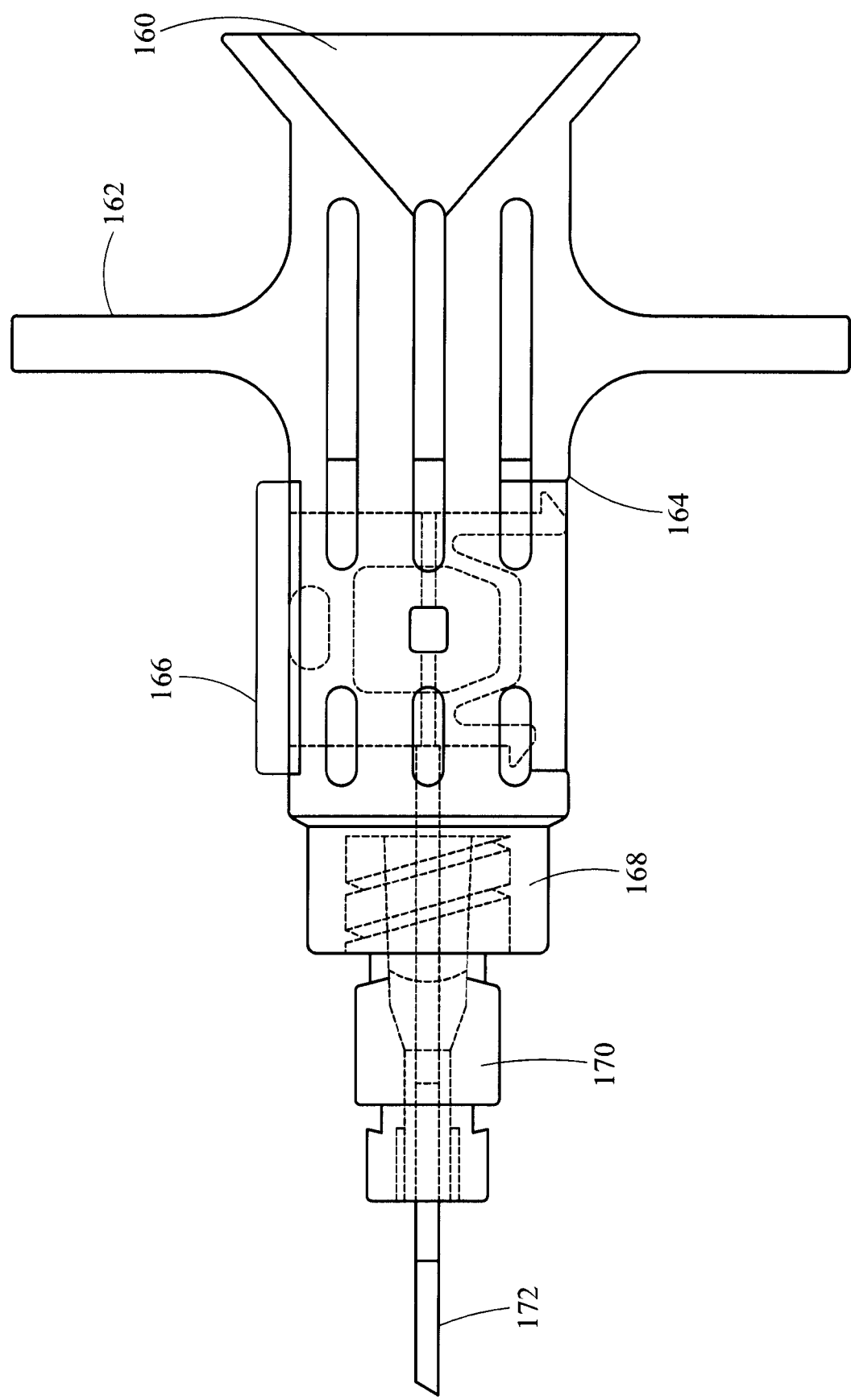
FIG. 7 illustrates a side view of an embodiment of a partially assembled drug depot storage and/or delivery device having a housing, a cannula that is attached to the housing, a drug cartridge containing a drug depot attached to the housing that is aligned with the drug delivery channel. In the embodiment shown, the device is ready for the insertion of a plunger and ready for drug delivery as the retaining member (e.g., ring member) has been removed from the housing or is in an open position and rotated away from the drug cartridge.

FIG. 7 illustrates a side enlarged view of an embodiment of a partially assembled drug depot storage and/or delivery device comprising a housing 164 having a first end 160 and a second end 168 and an opening having a drug cartridge 166 slid into the opening. The first end 160 of the housing is configured to receive at least the tip and body of a plunger. The plunger will contact the first end when the plunger is in the extended position. The second end 168 of the housing is configured to receive at least the tip of the plunger and allow passage of the drug depot out through it. This can be accomplished by sliding the plunger in the forward direction, which allows plunger body and tip to slide through an opening in the first end 160 and through the delivery channel and through the aligned channel of the drug cartridge, which pushes the drug depots out of the channel and into the delivery channel of the housing and out second end opening 168 into cannula or needle 172. The housing at the second end is configured to be attached to a cannula or needle 172 via a fitting means 170, which can be a snap fitting, a friction fitting, or a leur fitting.

The housing has an opening configured to receive drug cartridge 166, which is shown in this embodiment, further slid into the opening of the housing so that the lip of the drug cartridge contacts the housing. The drug cartridge 166 contains one or more drug depots. In this embodiment shown, the ring member has been rotated away from the drug cartridge 166 or is removed from the housing 164 all together. This allows the drug cartridge 166 to be further or completely slid into the housing, which aligns the channel of the drug cartridge and the delivery channel of the housing. This allows the user to push the plunger in a forward direction and deploy the drug depots out of the second opening 168 and into the cannula or needle 172 and the plunger can push the one or more drug depots out of the cannula or needle 172 and to the target tissue site. This can happen because the drug delivery channel of the housing and the channel of the drug cartridge are aligned.

In some embodiments, the drug cartridge 166 vertically slides in the opening of the housing to align the channel of the drug cartridge and the drug delivery channel. In this case, the ring member is removable from the housing or rotatable around the housing to remove it from the drug cartridge so as to allow alignment of the channel of the drug cartridge with the drug delivery channel. In some embodiments, the device may have handles 162 for easy grasping.

Figure 8:
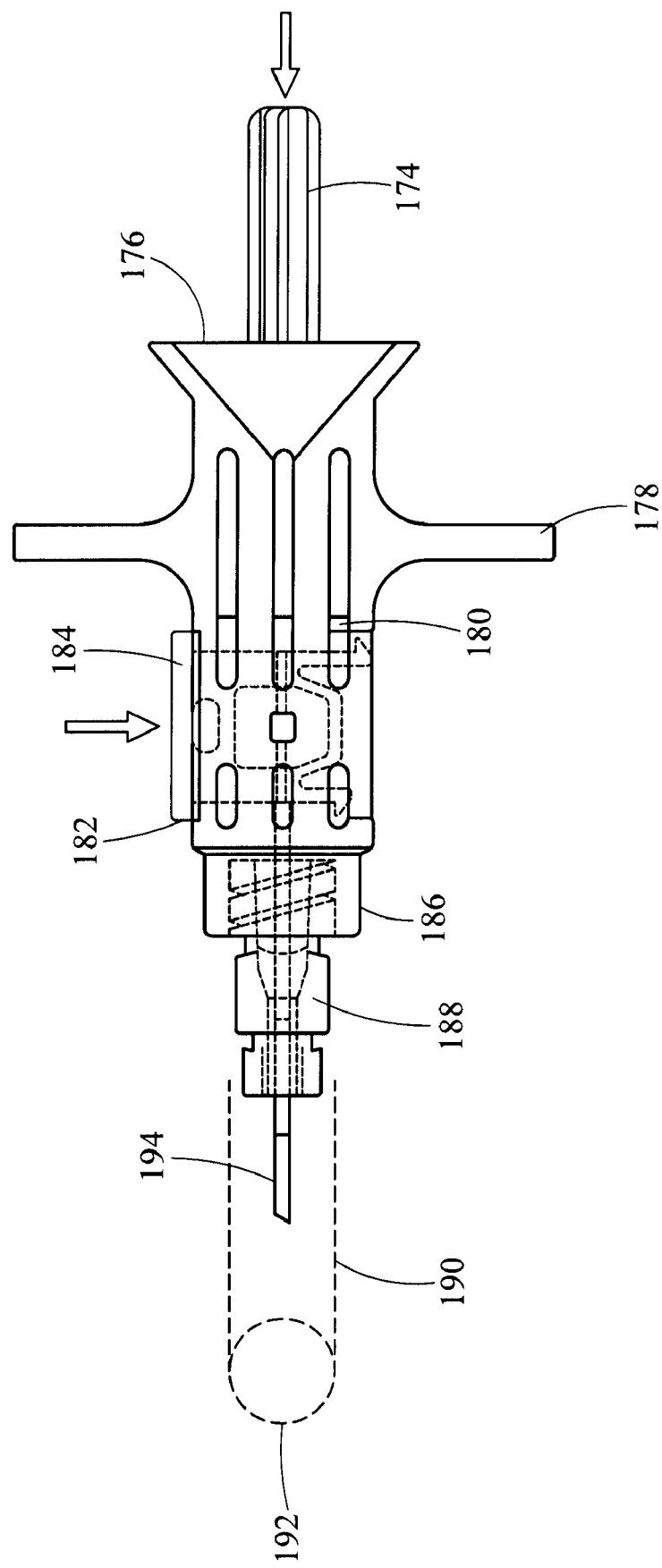
FIG. 8 illustrates a side view of an embodiment of an assembled drug depot storage and/or delivery device having a housing, a cannula that is attached to the housing and disposed in a sheath, a drug cartridge containing a drug depot attached to the housing that is aligned with the drug delivery channel, and the ring member has been removed from the housing or is rotated away from the drug cartridge in an open position. In this illustrated embodiment, the plunger is disposed in the housing and the device can deliver the drug depot by pushing the plunger.

FIG. 8 illustrates a side enlarged view of an embodiment of an assembled drug depot storage and/or delivery device comprising a housing 180 having a first end 176 and a second end 186 and an opening 182 having a drug cartridge 184 slid into the opening shown by the short dark arrow. The first end 176 of the housing is configured to receive at least the tip and body of a plunger. The plunger handle is shown as 174. The plunger will contact the first end when the plunger is in the extended position. The second end 186 of the housing is configured to receive at least the tip of the plunger and allow passage of the drug depot out through it. This can be accomplished by sliding the plunger in the forward direction (shown by the long dark arrow), which allows plunger body and tip to slide through an opening in the first end 174 and through the delivery channel and through the aligned channel of the drug cartridge, which pushes the drug depots out of the channel and into the delivery channel of the housing and out second end opening 186 into cannula or needle 194. There may also be a sheath 190 disposed at or near the target tissue site. In some embodiments, the plunger is longer than the cannula and needle and sheath. In this case, the plunger extends beyond the cannula, needle or sheath and can push the drug depots out opening 192 of the sheath and to the target tissue site. In the embodiment shown, the sheath has a larger diameter than the cannula or needle and the plunger. In some embodiments, the housing at the second end is configured to be attached to a cannula or needle 194 via a fitting means 188, which can be a snap fitting, a friction fitting, or a leur fitting.

The housing has an opening 182 configured to receive drug cartridge 184, which is shown in this embodiment, slid into the opening of the housing. The drug cartridge 184 contains one or more drug depots. In this embodiment shown, the ring member has been rotated away from the drug cartridge 184 or is removed from the housing 180 all together. This allows the drug cartridge 184 to be further or completely slid into the housing, which aligns the channel of the drug cartridge and the delivery channel of the housing. This allows the user to push the plunger in a forward direction and deploy the drug depots out of the second opening 186 and into the cannula or needle 194 and/or sheath 190 and the plunger can push the one or more drug depots out of the cannula or needle and/or sheath and to the target tissue site. This can happen because the drug delivery channel of the housing and the channel of the drug cartridge are aligned.

In some embodiments, the drug cartridge 184 vertically slides (shown by the short dark arrow) in the opening of the housing to align the channel of the drug cartridge and the drug delivery channel. In this case, the ring member is removable from the housing or rotatable around the housing to remove it from the drug cartridge so as to allow alignment of the channel of the drug cartridge with the drug delivery channel. In some embodiments, the device may have handles 178 for easy grasping.

Cannula or Needle or Sheath

The cannula or needle or sheath of the drug depot device is designed to cause minimal physical and psychological trauma to the patient. Cannulas or needles or sheaths include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The cannula or needle or sheath may optionally include one or more tapered regions. In various embodiments, the cannula or needle or sheath may be beveled. The cannula or needle or sheath may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle or sheath may also be non-coring and have a sheath covering it to avoid unwanted needle sticks.

The cannula or needle or sheath of the drug depot device has a diameter that is larger than the diameter of at least part of the plunger (e.g., tip, middle, etc.) to allow at least part of the plunger to be slidably received within the cannula or needle or sheath. In various embodiments, the diameter of the cannula or needle or sheath is substantially the same throughout. In other embodiments, the diameter of the needle or cannula or sheath becomes smaller approaching the distal end for drug delivery.

The dimensions of the hollow cannula or needle or sheath, among other things, will depend on the site for implantation. For example, the width of the epidural space is only about 3-5 mm for the thoracic region and about 5-7 mm for the lumbar region. Thus, the needle or cannula or sheath, in various embodiments, can be designed for these specific areas. Some examples of lengths of the cannula or needle or sheath may include, but are not limited to, from about 50 to 150 mm in length, for example, about 65 mm for epidural pediatric use, about 85 mm for a standard adult and about 150 mm for an obese adult patient. The thickness of the cannula or needle or sheath will also depend on the site of implantation. In various embodiments, the thickness includes, but is not limited to, from about 0.05 to about 1.655. The gauge of the cannula or needle or sheath may be the widest or smallest diameter or a diameter in between for insertion into a human or animal body. The widest diameter is typically about 14 gauge, while the smallest diameter is about 25 gauge. In various embodiments the gauge of the needle or cannula or sheath is about 17 to about 25 gauge.

In various embodiments, the plunger, cannula or needle or sheath or drug depot include markings that indicate location at or near the site beneath the skin. Radiographic markers can be included on the drug depot to permit the user to accurately position the depot into the site of the patient. These radiographic markers will also permit the user to track movement and degradation of the depot at the site over time. In this embodiment, the user may accurately position the depot in the site using any of the numerous diagnostic-imaging procedures. Such diagnostic imaging procedures include, for example, X-ray imaging or fluoroscopy. Examples of such radiographic markers include, but are not limited to, barium, calcium phosphate, and/or metal beads.

In various embodiments, the needle or cannula or sheath may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

In various embodiments, the drug cartridge contains one or more drug depots in the form of drug pellets loaded within the channel of the drug cartridge, when only the plunger is moved to the extended position, the drug cartridge will remain within the housing and the channel of the drug cartridge will guide the tip of the plunger longitudinally and the drug pellet will be released from it when it is in the extended position. A subsequent or second pellet may be administered by pushing the plunger further to release a second drug depot or a second drug cartridge can be inserted. Alternatively, the device can be repositioned and another drug depot delivered to the target tissue site. In this way, sequential delivery of a drug can be accomplished. Thus, the above procedure (e.g., repositioning the needle, sliding the drug cartridge in position to align the channels, inserting the plunger, delivering the drug depot) can be repeated multiple times to deliver multiple drug depots to the target tissue site.

In various embodiments, surrounding the opening of the proximal end of the cannula or needle or sheath is a generally cylindrical hub having an engagement means (shown as internal threading) for engaging the housing. Engagement means include, but are not limited to, threading, tracks, clips, ribs, projections, and the like that allow a secure connection between the housing, ring, drug cartridge, plunger, and/or the proximal end of the cannula, needle or sheath. For example, in various embodiments the engagement means may be a luer lock connection, where the cannula has mating threads that mate with the threads disposed on or in the housing.

Housing

The housing may be of various shapes including, but not limited to, rectangular, square, cylindrical or round such that the housing allows for the affixation to the cannula or needle or sheath as well as the drug cartridge, ring member and the plunger.

The housing may comprise a variety of materials, such as, for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof.

Like the cannula or needle or sheath, in various embodiments, the housing may have dose indicator markings (e.g., numbers, lines, letters, radiographic markers, etc.) to indicate the number of drug depots delivered. In various embodiments, the plunger includes markings that indicate location at or near the site beneath the skin.

The housing may have contours and allow easy grasping of the device during use for insertion of the drug depot. The housing can be angled for right and left hand users or can be generic for both hands. In various embodiments, the housing can comprise a first opening, a middle opening, and a lower opening. The first, middle and second openings allow a plunger to slide through the openings. The middle opening of the housing, in various embodiments, will receive the drug cartridge and the user can align the channels of the drug cartridge with the channels of the first, middle and second openings so that the plunger can pass through and deliver the drug depot.

The housing can have mating members, such as for example, recesses, projections, openings, and/or ledges, that facilitate attachment and removal of complementary mating members such as for example, recesses, projections, openings, and/or ledges of the drug cartridge, ring member, plunger, needle, cannula and/or sheath.

Plunger

Although the first end of the plunger is shown as a knob, it will be understood that the knob can be a top, dial, cap, handle or any member that allows the user to utilize the plunger. The plunger has a second end that includes a tip, which is capable of moving the drug depot within the drug cartridge, housing, cannula, needle, and/or sheath. In other embodiments, the tip of the plunger is sufficiently pointed so that it is capable of insertion to the site beneath the skin of the patient and the cannula or needle or sheath is blunted and used to guide the drug depot to the site.

In some embodiments, at least a portion of the plunger (e.g., tip, body) has a diameter less than the cannula, needle, sheath, channel of the drug cartridge, and/or delivery channel of the housing so that it can be slidably received therein. The plunger may be longer, the same size, or smaller in length than the cannula or needle or sheath. In embodiments where the plunger extends from the distal end of the cannula or needle or sheath, the plunger is usually longer than the cannula or needle or sheath. In some embodiments, the tip of the plunger can be sharp or blunt.

The plunger may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The plunger may optionally include one or more tapered regions.

Like the cannula or needle or sheath, or housing or drug cartridge, or ring member, in various embodiments, the plunger may have dose indicator markings (e.g., numbers, lines, letters, radiographic markers, etc.) to indicate the number of drug depots delivered. In various embodiments, the plunger includes markings that indicate location at or near the site beneath the skin.

The plunger tip, which may be a complementary shape to the drug depot (e.g., drug pellet), allows the plunger tip to snuggly fit within the end of the drug depot for easier drug delivery. The drug depot may have a rounded end for easier insertion at the desired site.

Drug Depot

In various embodiments, the device comprises a drug depot. A drug depot comprises a physical structure to facilitate implantation and retention in a desired site (e.g., a synovial joint, a disc space, a spinal canal, a tissue of the patient, etc.). The drug depot also comprises the drug. The term "drug" as used herein is generally meant to refer to any substance that alters the physiology of the patient. The term "drug" may be used interchangeably herein with the terms "therapeutic agent", "therapeutically effective amount", and "active pharmaceutical ingredient". It will be understood that a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 1 mm to about 5 cm from the implant site.

Suitable drugs include, for example, antimicrobials and/or antibiotics biocidal/biostatic sugars such as dextran, glucose, etc.; amino acids; peptides; vitamins; inorganic elements; co-factors for protein synthesis; hormones; living cells such as mesenchymal stem cells, natural extracts, genetically engineered living cells or otherwise modified living cells; DNA delivered by plasmid or viral vectors; tissue transplants; demineralized bone powder; autogenous tissues such as blood, serum, soft, bone morphogenic proteins (BMPs); osteoinductive factor; fibronectin (FN), osteonectin (ON); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; amelogenins, growth differentiation factors (e.g., GDF-5) transforming growth factor (TGF-beta); insulin-like growth factor (IGF-1); platelet derived growth factors (PDGF); fibroblast growth factors (FGF, bFGF, etc.); periodontal ligament chemotactic factor (PDLGF); somatotropin; immuno-suppressants; permeation enhancers, e.g., fatty acid esters such as laureate, myristate and stearate monoesters of polyethylene glycol, enamine derivatives, alpha-keto aldehydes, etc.; or nucleic acids. When employed, the total amount of drug can represent from about 0.1 to about 60 weight percent of the drug depot.

Exemplary drugs suitable for use in the drug depot, include, but are not limited to an anti-inflammatory agent, analgesic agent, or osteoinductive growth factor or a combination thereof. Anti-inflammatory agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or protein inhibitors of TNF, such as etanercept, Remicade, IL-1, such as Kineret®, p38, RANK, RANKL, or a combination thereof.

Suitable osteoinductive factors include, but are not limited to, a bone morphogenetic protein, a growth differentiation factor, a LIM mineralization protein or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof. Analgesics also include agents with analgesic properties, such as for example, amitriptyline, carbamazepine, gabapentin, pregabalin, clonidine, or a combination thereof.

A "depot" includes but is not limited to capsules, microspheres, particles, coating, matrices, wafers, pills, pellets or other pharmaceutical delivery compositions. In various embodiments, the depot may comprise a bioerodible, a bioabsorbable, and/or a biodegradable biopolymer that may provide immediate release, or sustained release of the drug. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations. In various embodiments, the drug depot comprises poly(lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone or a combination thereof.

In various embodiments, the drug depot comprises drug pellets loaded with a therapeutically effective amount of the therapeutic agent, wherein the pellets are injected into a target tissue site (e.g., a synovial joint, a disc space, a spinal canal, or a soft tissue surrounding the spinal canal, bone, muscle, soft tissue, etc.). In various embodiments, the drug pellets comprise a gel in viscous form and microspheres loaded with a therapeutic agent, wherein the combination of gel and microspheres are positioned into a synovial joint, disc space, a spinal canal, or a soft tissue surrounding the spinal canal of a subject.

A "therapeutically effective amount" is such that when administered, the drug results in alteration of the biological activity, such as, for example, inhibition of inflammation, reduction or alleviation of pain, improvement in the condition, etc. The dosage administered to a patient can be as single or multiple doses depending upon a variety of factors, including the drug's pharmacokinetic properties, the route of administration, patient conditions and characteristics (sex, age, body weight, health, size, etc.), extent of symptoms, concurrent treatments, frequency of treatment and the effect desired.

In one exemplary embodiment, the drug depot is in the form of a pellet. The pellet can be any shape, such as for example, bullet shaped, spherical, substantially spherical, flaked, rod shaped, square, oval, etc. In various embodiments, the drug pellet has an aspect ratio (a ratio of the length of the pellet divided by the width found at an angle of 90° in respect to the length) which is less than about 1.4 to about 1.05. In some embodiments, the pellets are from about 0.5 mm to about 5 mm in length. In some embodiments, the pellets are from about 0.5 mm to about 5 mm in diameter.

The proximal end of the drug pellet may allow the plunger tip to snuggly fit within the proximal end of the drug pellet for easier drug delivery. The distal end of the drug pellet may be rounded for easier insertion at the site.

In various embodiments, the drug pellet comprises a bullet-shaped body that is made from a biodegradable material. In alternative embodiments, the body of the pellet may be made from a non-biodegradable material. A non-biodegradable body could be a porous hollow chamber filled with the therapeutic agent alone or incorporated into a degradable polymer. It may be desirable to make the body non-degradable to be able to retrieve it after it has released its contents. Non-limiting examples of suitable biodegradable materials for the pellet body include polyorthoesters (POE), polylacticglycolic acid (PLGA) polysacharides (Saber technology), polycapralactone, polyfumarate, tyrosine polycarbonate, etc. The body may be solid, and the therapeutic agent may be dispersed throughout the material that forms the body. The dispersal of the therapeutic agent may be even throughout the body. Alternatively, the concentration of the therapeutic agent may vary throughout the body. As the biodegradable material of the body degrades at the site, the therapeutic agent is released.

Procedures for making pellets include, but are not limited to, extrusion-spheroidization, for spherical pellets where the active pharmaceutical ingredient (API) and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, cylindrical extrudate of uniform shape and size. The size of the opening in the screen or die dictate resultant pellet size. The extrudate is fed onto a rotating disk, which may be smooth or may contain a grid (waffled, grooved, etc.) and the extrudate breaks into small cylinders, which in time are rounded into spherically shaped solids. Subsequently, the pellets are dried to the desired residual moisture content, typically in a fluid bed dryer. Any oversized or undersized product is removed by sieving, and the resulting pellets have a narrow size distribution.

In various embodiments, the API is layered on the solid core of the pellet by solution or suspension layering or powder layering techniques. In solution or suspension layering, an API and any inactive ingredients (excipients, binders, etc.) are suspended or dissolved in water or an organic solvent. The resulting liquid is sprayed onto the outside of a core particle, which may include, for example, non-pareil sugar seed (sugar sphere), microcrystalline cellulose pellets and the like, to make the pellet having the desired potency. Solution or suspension layering may be conducted using a wide variety of process techniques, for example, by fluidized bed, Wurster bottom spray techniques, or the like. When the desired potency has been achieved, pellets are dried to the desired residual moisture content. Any oversized or undersized product may be removed by sieving, and the resulting pellets are narrow in size distribution.

Powder layering may also be used to make the drug pellets. Powdered layering involves the application of a dry powder to the pellet core material. The powder may contain the drug, or may include excipients such as a binder, flow aid, inert filler, and the like. In the powder layering technique a pharmaceutically acceptable liquid, which may be water, organic solvent, with or without a binder and/or excipients, is applied to the core material while applying the dry powder until the desired potency is achieved. When the desired potency has been achieved, the pellets may be seal coated to improve their strength, and are then dried to the desired moisture content. Any oversized or undersized product is removed by sieving, and the resulting pellets are narrow in size distribution.

In one embodiment, the pellet is made using a core of biodegradable material, such as, for example, polyglactin, polylactone, polylactide, etc. The core is then coated with a thin layer of the API, such as an anti-inflammatory agent, analgesic agent, etc. by solution, suspension, or powdered layering until the desired potency is achieved.

In various embodiments, the drug pellets can be different sizes, for example, from about 0.5 mm to 5 mm in length and have a diameter of from about 0.01 to about 2 mm. The layer or layers will each have a layer thickness of from about 0.005 to 1.0 mm, such as, for example, from 0.05 to 0.75 mm. The channel(s) of the drug cartridge and delivery channel(s) of the housing are often larger than the drug depot dimensions to keep the drug depot within the drug channels.

Like the cannula, needle, sheath, drug cartridge, or plunger, in various embodiments, the drug depot (e.g., pellet) may have dose indicator markings (e.g., numbers, lines, letters, radiographic markers, etc.) to indicate the number of drug depots delivered. In various embodiments, radiopaque marks are positioned on the depot at opposite ends of the depot to assist in determining the position of the depot relative to the treatment site. For example, the radiopaque marker could be a spherical shape or a ring around the depot.

Drug Cartridge

In various embodiments, the drug depot is stored in a drug cartridge. The drug cartridge comprises one or more channels, each channel capable of storing one or more drug depots. Each channel isolates the one or more drug depots from the outside environment when included with the housing that contains the drug depots and reduces the chance or prevent them from falling out of the cartridge.

In various embodiments, the drug cartridge can slide into the housing opening of the drug depot storage and delivery device. For example, the drug cartridge can be any shape (e.g., circular, rectangular, square shaped, etc.) and slide into a complementary opening of the housing and the ring member is then attached to the housing to keep the cartridge in a closed position and not aligned with the delivery channel of the housing. In various embodiments, the drug cartridge is linear and is slidably receivable through the opening of the housing such that the cartridge is perpendicular to the housing. For example, the drug cartridge may be a rectangular shape and slide within the opening of the housing at a position perpendicular to the plunger. To deliver the drug depot, the cartridge slides with the housing to align with cannula and plunger. The plunger then slides through the cannula to deliver the drug depot through the cannula and out to the target site as discussed above in FIGS. 1-8.

In various embodiments, the drug cartridge may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or a combination thereof. In various embodiments, the drug cartridge is not biodegradable.

In some embodiments, the drug cartridge comprises 1, 2, 3, 4, 5, 6, 7, 8, 9, 10, 11, 12, 13, 14, 15, 16, 17, 18, 19, and 20 drug depots and/or channels. The channels and/or drug depots can be spaced an equal distance from each other. For example, the drug channels or drug depots can be spaced 0.5 mm, or 1 mm, or 5 mm, or 1 cm to about 2 cm from each other.

FIG. 3 illustrates an exemplary embodiment of a drug cartridge that contains the drug depot. The drug cartridge can have mating members, such as for example, recesses, projections, openings, and/or ledges, that facilitate attachment and removal of complementary mating members such as for example, recesses, projections, openings, and/or ledges of the housing, ring member, plunger, needle, cannula and/or sheath.

Retaining Member

In various embodiments, the drug storage and delivery device comprises a retaining member. The retaining member can be a ring, clip, stick, plate, shaft, wand, board, bar, pin or other structure that can attach to the housing and contact the cartridge to hold it in position. In some embodiments, the retaining member comprises a ring member. The retaining member (e.g., ring member) is configured to reduce or prevent movement of the drug cartridge and attach to the housing by mating openings, recesses or projections. In this way, retaining member functions as a safety ring and prevents or reduces the chance that the drug cartridge will move in a position that would allow the drug depots to prematurely discharge from the housing or fall out of the drug cartridge. The safety ring also reduces or prevents the chances that the drug cartridge will fall out of the housing.

In some or the same embodiment, the retaining member is a ring member and comprises projections or arms that allow it to be removably attach to the housing and the drug cartridge. For example, one arm of the ring member can attach to the housing and the second arm can attach to the drug cartridge and hold it in position. The ring member may have a diameter that is smaller than the housing and the ring member can be pushed onto housing, which forces the ring's arms around the housing. This can be a force-fit, friction fit, snap fit, spring fit type, or other type of coupling means.

In some embodiments, the ring member is rotatable around the housing and the user can rotate the safety ring around the housing. The user can then rotate the ring member into a desired position, which allows containment of the drug depots in a locking position or closed position or deployment of the drug depots in an open position.

In various embodiments, the ring member may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or a combination thereof. In various embodiments, the ring member is not biodegradable.

The ring member can have mating members, such as for example, recesses, projections, openings, and/or ledges, that facilitate attachment and removal of complementary mating members such as for example, recesses, projections, openings, and/or ledges of the housing, drug cartridge, plunger, needle, cannula and/or sheath.

Bulking Agent

In various embodiments, the drug depots can be further secured in the drug cartridge by use of a bulking agent. The bulking agent may be added to the drug depot to ensure the drug depot is secure within the channel, such that the drug depot is released when the plunger is engaged to dislodge the drug depot from the cartridge. In some embodiments, the bulking agent is added to the channel before the drug depot is added to the channel. In some embodiments, the drug depot is added to the drug channel first and then the drug depot is added to the channel. In other embodiments, the bulking agent and the drug depot are added to the drug channel together.

In some embodiments, the bulking agent can be penetrated and can be cored by the plunger and/or depot in order to release the drug depot. A bulking agent includes an excipient, which provides bulk, in addition to the housing, ring member, and/or drug cartridge, and structure to the drug depot and holds the drug depot in position within the channel. In some embodiments, the bulking agent prevents unwanted movement, contaminants (e.g., moisture), and breakage of the drug depot. In some embodiments, the bulking agent fills the space within the channel so that there is little or no repositioning of the drug depot during delivery. Examples of suitable bulking agents include hydrophilic excipients, such as, water soluble polymers; sugars, such as mannitol, sorbitol, xylitol, glucitol, ducitol, inositiol, arabinitol, arabitol, galactitol, iditol, allitol, maltitol, fructose, sorbose, glucose, xylose, trehalose, allose, dextrose, altrose, lactose, talc, zinc oxide, starch, hydroxyethylstarch (hetastarch), cellulose, cyclodextrins, glycine, fructose, gulose, idose, galactose, talose, ribose, arabinose, raffinose, xylose, lyxose, sucrose, maltose, lactose, lactulose, fucose, rhamnose, melezitose, maltotriose, raffinose, altritol, their optically active forms (D- or L-forms) as well as the corresponding racemates; inorganic salts, both mineral and/or mineral organic, such as, calcium salts, such as the lactate, gluconate, glycerylphosphate, citrate, phosphate monobasic and dibasic, succinate, sulfate and tartrate, as well as the same salts of aluminum and magnesium; carbohydrates, such as, the conventional mono- and di-saccharides as well as the corresponding polyhydric alcohols; proteins, such as, albumin; amino acids, such as glycine; emulsifiable fats or polyvinylpyrrolidone or a combination thereof. Exemplary bulking agents include glycine, mannitol, dextran, dextrose, lactose, sucrose, polyvinylpyrrolidone, trehalose, glucose, wax, agar, agarose, gel-vitamin or combinations thereof. The bulking agent may be in solid, semisolid, or liquid form. In various embodiments, the bulking agent is in a powdered form.

In some embodiments, the particle size of the solid or semi-solid bulking agents range from about 10 microns to about 1500 microns in diameter, or from about 150 microns to about 1100 microns in diameter, or from about 500 microns to about 900 microns in diameter. The size of the particles chosen for a particular application will be determined by a number of factors. Smaller particles are easier to inject with a smaller gauge size needle. The size of the particles used in a particular procedure will include consideration of the procedure employed, disease progression, the degree of degradation of the affected region, patient size, the disposition of the patient, and the preferences and techniques of the doctor performing the procedure.

In some embodiments, the bulking agent includes a bioerodible, a bioabsorbable, and/or a biodegradable biopolymer like the one or more depots. Examples of suitable materials include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), mPEG, poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, $\epsilon$-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. In various embodiments, the bulking agent comprises poly(lactide-co-glycolide) (PLGA), polylactide (PLA), polyglycolide (PGA), D-lactide, D,L-lactide, L-lactide, D,L-lactide-$\epsilon$-caprolactone, D,L-lactide-glycolide-$\epsilon$-caprolactone or a combination thereof.

The drug device components (e.g., cannula or needle, plunger, housing, ring member, engagement means, etc.) may be lightweight, disposable and sterilizable such that when the device is assembled (e.g., the drug cartridge is attached to the housing), the weight of the device does not substantially increase. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, the drug cartridge provides the advantages of ease of manufacturing in the terminal sterilization process. If the drug depots (e.g., drug pellets) are pre-loaded in the manufacturing process, gamma radiation may be required at higher doses to sterilize the drug depot loaded in the cannula or needle. This is particularly so when the cannula or needle is made from steel or metal. Thus, to sterilize the loaded depot, the dose of gamma rays must be high enough to penetrate the metal, which may destroy the API in the drug depot. By providing a drug cartridge, for example, made of plastic, the drug cartridge and drug depots in the cartridge can be sterilized, without destroying the API and then subsequently loaded by the manufacturer or the user (e.g., surgeon, physician, nurse, etc.) into the housing and the ring member can be attached to hold the drug cartridge in position and the drug depots will be contained. Further, loading the drug cartridge into the housing to align the drug depots for delivery can be easier. This is particularly so when dealing with multi-dose drug pellets that are relatively small (e.g., 0.5 mm, 0.7 mm, 1 mm, 1.5 mm, 2 mm, 2.5 mm, 3.0 mm, 3.5 mm, 4.0 mm, 4.5 mm to 5 mm), the user typically cannot grasp these small pellets and load them into the device. By providing them in a drug cartridge, the user does not have to substantially manipulate the individual drug pellets and the risk of contaminating the pellets particularly with sterilized pellets is reduced because the larger drug cartridge is much easier to manipulate.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot includes a gelatin capsule.

Other methods may also be used to sterilize one or more components of the device, including, but not limited to, gas sterilization, such as, for example, with ethylene oxide or steam sterilization.

In some embodiments, the device (e.g., housing, ring member, drug cartridge, plunger, cannula or needle, etc.) comprises indicator means that can be identified with dose marking or other markings to give a visual signal to the user that the drug depot is ready for administering.

In some embodiments, the housing, drug cartridge, ring member, cannula, needle, and/or sheath are transparent so the user can see the position of the plunger and/or the drug depot in the channel of the drug cartridge or the delivery channel of the housing, for example, if they are aligned for delivery. Thus, indicator markings, in this embodiment, are not needed.

In various embodiments, a kit is provided which may include additional parts along with the drug depot device combined together to be used to implant the drug depot. The kit may include the drug depot device in a first compartment (loaded or unloaded with the drug cartridge) and having the ring member attached. The second compartment may include other drug cartridges and any other instruments needed for the implant. A third compartment may include gloves, drapes, wound dressings and other procedural supplies for maintaining sterility of the implanting process, as well as an instruction booklet. A fourth compartment may include additional cannulas, needles and/or sheath. Each tool may be separately packaged in a plastic pouch that is radiation sterilized. A cover of the kit may include illustrations of the implanting procedure and a clear plastic cover may be placed over the compartments to maintain sterility.

Methods of Use

In various embodiments, a method of delivering a drug depot to a target tissue site beneath the skin is provided, the method comprising inserting a sheath at the target tissue site, the sheath having a proximal end and a distal end, the proximal end of the sheath having an opening to receive a drug depot, the distal end of the sheath having an opening for passage of the drug depot; inserting a cannula into the sheath, the cannula connected to a drug delivery device, the drug delivery device having a housing having a first end configured to receive a plunger, a second end configured to receive a cannula, an opening disposed in the housing between the first and second ends, and a delivery channel disposed within the housing and configured to receive the plunger; a drug cartridge configured to be disposed in the opening of the housing between the first and second ends of the housing, the drug cartridge having a mating member and comprising a drug depot disposed in a channel of the drug cartridge, the channel of the drug cartridge configured to receive at least a tip of the plunger and align with the delivery channel of the housing; and a ring member configured to attach to the housing and mate with the mating member of the drug cartridge to prevent alignment of the channel of the drug cartridge with the delivery channel of the housing when the ring member is in a closed position so as to allow storage of the drug depot, and the ring member configured to allow alignment of the channel of the drug cartridge with the delivery channel of the housing when the ring is in an open position so as to allow delivery of the drug depot from the drug cartridge by the plunger; moving the ring member to the open position or removing the ring member from the housing; and moving the tip of the plunger so as to cause delivery of the drug depot from the drug cartridge into at least the cannula or sheath and to the target tissue site by moving the plunger.

In some embodiments, to deliver the one or more drug depots to a target tissue site, a sheath is not needed, and the cannula or needle can be used to penetrate the skin and the user can move it to the target tissue site. In other embodiments, a sheath can be inserted at or near the target tissue site; the sheath can contain a stylet to plug the hole of the sheath. The sheath can be used to withdraw blood and other bodily fluids when the stylet is withdrawn from the sheath. Next, the cannula or needle of the drug depot device can be inserted into the sheath after the stylet has been removed and the ring member removed or rotated to allow the user to further slide the drug cartridge into the housing to align the one or more drug depots and the plunger can now push the drug depots out of the device, and in some embodiments, where a long plunger is used, through the sheath and to the target tissue site. It will be understood by those of ordinary skill in the art that the cartridge can be aligned in the housing before the cannula or needle is inserted into the sheath.

In some embodiments, a balloon type device is used to move apart select tissue, which creates and maintains space in the tissue for the one or more drug depots to be implanted into the tissue that has been spaced apart.

In various embodiments, the seal between the plunger tip and the cannula or needle can be air tight so that when the cannula or plunger penetrates the skin, at times, fluid (e.g., blood, spinal fluid, synovial fluid, etc.) may be drawn up into the cannula or needle. This fluid will be expelled when the plunger is re-inserted into the cannula or needle and the drug depot is released.

The device may be used for localized and/or targeted delivery of the drug depot to a patient to treat a disease or condition such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, bone muscles, and the like.

In various embodiments, the drug depot device is used to treat pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

The device can be used for localized delivery of the one or more drug depots. "Localized" delivery includes, delivery where one or more drugs are deposited within a tissue, for example, a nerve root of the nervous system or a region of the brain, or in close proximity (within about 10 cm, or preferably within about 5 cm, for example) thereto. "Targeted delivery system" provides delivery of one or more drugs depots in a quantity of pharmaceutical composition that can be deposited at the target site as needed for treatment of pain, inflammation or other disease or condition.

It will be understood by those of ordinary skill in the art that after delivery of the first drug pellet, the cannula or needle can be re-positioned and another pellet can be delivered to the target area. Thus, the device allows for sequential delivery of multiple pellets and one can triangulate these pellets around a pain generator or other target tissue site. For example, if a target tissue site generates pain, the physician can place multiple drug pellets containing an anti-inflammatory and/or analgesic agent around this pain generator.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A device for storing a drug depot, the device comprising:
   a housing having a first end configured to receive a plunger, a second end configured to receive a cannula, an opening disposed in the housing between the first and second ends and configured to receive a drug cartridge containing a drug depot, and a delivery channel disposed within the housing and configured to receive the plunger and the drug depot from the drug cartridge, the drug cartridge having an opening, recess or projection and comprising a channel to receive the drug depot and the plunger and align with the delivery channel of the housing to allow delivery of the drug depot from the drug cartridge by the plunger; and
   a retaining member configured to attach to the housing and the opening, recess or projection of the drug cartridge to prevent alignment of the channel of the drug cartridge with the delivery channel of the housing so as to store the drug depot.

2. A device according to claim 1, further comprising a cannula attached to the second end of the housing, the cannula having a proximal end and a distal end, the proximal end of the cannula having an opening to receive at least a tip of the plunger, wherein the tip of the plunger is slidably within each of the first end, the delivery channel, the second end of the housing and the channel of the drug cartridge, when the drug delivery channel is aligned with the channel of the drug cartridge or wherein the retaining member further comprises a ring, clip, pin, rod, stick, plate, shaft, wand, board, bar, or pin.

3. A device according to claim 1, wherein the retaining member is a safety ring and comprises a projection configured to mate with the opening of the drug cartridge so as to reduce or prevent alignment of the channel of the drug cartridge with the delivery channel of the housing.

4. A device according to claim 1, wherein the retaining member comprises upper and lower projections rotatable around the housing and a center projection or recess configured to mate with a recess or projection in the housing, and at least one of the projections configured to mate with the opening of the drug cartridge so as to store the drug depot within the drug cartridge and reduce or prevent alignment of the channel of the drug cartridge with the delivery channel of the housing.

5. A device according to claim 1, wherein the drug cartridge is configured to slide in the opening of the housing and align the channel of the drug cartridge with the delivery channel of the housing so that at least a portion of the plunger can slide within the delivery channel and the channel of the drug cartridge to allow delivery of the drug depot from the drug cartridge and out of the second end of the housing by pushing the plunger.

6. A device according to claim 5, wherein the drug cartridge comprises a first recess or projection and a second recess or projection configured to mate with a first complementary recess or projection and a second complementary recess or projection of the housing so as to lock the drug cartridge in position when the delivery channel of the housing and the channel of the drug cartridge are aligned.

7. A device according to claim 6, wherein the drug cartridge comprises first and second projections configured to attach to complementary first and second recesses of the housing, the first projection of the cartridge having a length longer than the second projection so as to prevent the drug cartridge from falling out of the housing.

8. A device according to claim 6, wherein at least one of (i) the plunger slides along a longitudinal axis in the channel of the drug cartridge and the drug delivery channel when the channel of the drug cartridge and the drug delivery channel are aligned; (ii) the drug cartridge vertically slides in the opening of the housing to align the channel of the drug cartridge and the drug delivery channel; or (iii) the retaining member is removable from the housing or rotatable around the housing to remove it from the drug cartridge so as to allow alignment of the channel of the drug cartridge with the drug delivery channel.

9. A device according to claim 1, wherein the drug cartridge contains a plurality of sterilizable and biodegradable drug depots disposed in the channel of the drug cartridge.

10. A device according to claim 1, wherein the second end of the housing comprises a leur fitting and the cannula is attached to the leur fitting.

11. A device according to claim 1, wherein the housing further comprises a port fluidly connected to the delivery channel to deliver a liquid.

12. A device for delivering a drug depot to a site beneath the skin of patient, the device comprising:
   a housing having a first end configured to receive a plunger, a second end configured to receive a cannula, an opening disposed in the housing between the first and second ends, and a delivery channel disposed within the housing and configured to receive the plunger;
   a drug cartridge configured to be disposed in the opening of the housing between the first and second ends of the housing, the drug cartridge having a mating member and comprising a drug depot disposed in a channel of the drug cartridge, the channel of the drug cartridge configured to receive at least a tip of the plunger and align with the delivery channel of the housing; and
   a ring member configured to attach to the housing and mate with the mating member of the drug cartridge to prevent alignment of the channel of the drug cartridge with the delivery channel of the housing when the ring member is in a closed position so as to allow storage of the drug depot, and the ring member configured to allow alignment of the channel of the drug cartridge with the delivery channel of the housing when the ring is in an open position so as to allow delivery of the drug depot from the drug cartridge by the plunger.

13. A device according to claim 12, further comprising a cannula attached to the second end of the housing, the cannula having a proximal end and a distal end, the proximal end of the cannula having an opening to receive at least a tip of the plunger, wherein the tip of the plunger is slidably within each of the first end, the delivery channel, the second end of the housing and the channel of the drug cartridge, when the drug delivery channel is aligned with the channel of the drug cartridge and the drug cartridge is slidably disposed in the opening of the housing.

14. A device according to claim 12, wherein the mating member of the drug cartridge comprises a recess, projection or opening that mates with a complementary recess, projection or opening of the ring member to reduce or prevent alignment of the channel of the drug cartridge with the delivery channel of the housing when the ring member is in the closed position.

15. A device according to claim 12, wherein the ring member comprises upper and lower projections rotatable around the housing and a center projection or recess configured to mate with a recess or projection in the housing, and at least one of the projections configured to mate with the mating member of the drug cartridge when the ring member is in a closed position so as to reduce or prevent alignment of the channel of the drug cartridge with the delivery channel of the housing to store the drug depot.

16. A device according to claim 12, wherein the drug cartridge is configured to slide in the opening of the housing and align the channel of the drug cartridge with the delivery channel of the housing so that at least a portion of the plunger can slide within the delivery channel and the channel of the drug cartridge to allow delivery of the drug depot from the drug cartridge and out of the second end of the housing by pushing the plunger in a forward direction.

17. A device according to claim 16, wherein the mating member of the drug cartridge comprises a first recess or projection and a second recess or projection configured to mate with a first complementary recess or projection and a second complementary recess or projection of the housing so as to lock the drug cartridge in position when the delivery channel of the housing and the channel of the drug cartridge are aligned.

18. A method of delivering a drug depot to a target tissue site beneath the skin, the method comprising:
 inserting a cannula at the target tissue site, the cannula having a proximal end and a distal end, the proximal end of the cannula having an opening to receive a drug depot, the distal end of the cannula having an opening for passage of the drug depot, the cannula connected to a drug delivery device, the drug delivery device having a housing having a first end configured to receive a plunger, a second end configured to receive the cannula, an opening disposed in the housing between the first and second ends, and a delivery channel disposed within the housing and configured to receive the plunger; a drug cartridge configured to be disposed in the opening of the housing between the first and second ends of the housing, the drug cartridge having a mating member and comprising a drug depot disposed in a channel of the drug cartridge, the channel of the drug cartridge configured to receive at least a tip of the plunger and align with the delivery channel of the housing; and a ring member configured to attach to the housing and mate with the mating member of the drug cartridge to prevent alignment of the channel of the drug cartridge with the delivery channel of the housing when the ring member is in a closed position so as to allow storage of the drug depot, and the ring member configured to allow alignment of the channel of the drug cartridge with the delivery channel of the housing when the ring is in an open position so as to allow delivery of the drug depot from the drug cartridge by the plunger;
 moving the ring member to the open position; and
 moving the tip of the plunger so as to cause delivery of the drug depot from the drug cartridge into at least the cannula and to the target tissue site by moving the plunger.

19. A method according to claim 18, wherein at least one of (i) the plunger slides along a longitudinal axis in the channel of the drug cartridge and the drug delivery channel when the channel of the drug cartridge and the drug delivery channel are aligned; (ii) the drug cartridge vertically slides in the opening of the housing to align the channel of the drug cartridge and the drug delivery channel; (iii) the ring member is removable from the housing or rotatable around the housing to remove it from the mating member of the drug cartridge so as to allow alignment of the channel of the drug cartridge with the drug delivery channel; or (iv) a sheath is inserted into the target tissue before the cannula.

20. A method according to claim 18, wherein the drug depot is delivered to the target tissue site by sliding at least the tip of the plunger along a longitudinal axis of the cannula thereby pushing the drug depot through the channel of the drug cartridge into the delivery channel of the housing and through the cannula and sheath.

* * * * *